US012745980B2

(12) United States Patent
Fenster et al.

(10) Patent No.: US 12,745,980 B2
(45) Date of Patent: Sep. 29, 2026

(54) WEARABLE 3D ULTRASOUND-BASED WHOLE BREAST IMAGING SYSTEM

(71) Applicant: Aaron Fenster, London (CA)

(72) Inventors: Aaron Fenster, London (CA); Jeffrey Scott Bax, Lucan (CA); David Ronald Tessier, London (CA); Claire Keun Sun Park, Edmonton (CA)

(73) Assignee: Aaron Fenster, London (CA)

( * ) Notice: Subject to any disclaimer, the term of this patent is extended or adjusted under 35 U.S.C. 154(b) by 0 days.

(21) Appl. No.: 19/174,345

(22) Filed: Apr. 9, 2025

(65) Prior Publication Data

US 2025/0261930 A1 Aug. 21, 2025

Related U.S. Application Data

(63) Continuation of application No. 18/136,926, filed on Apr. 20, 2023, now abandoned.

(60) Provisional application No. 63/335,857, filed on Apr. 28, 2022.

(51) Int. Cl.
*A61B 8/00* (2006.01)
*A61B 8/08* (2006.01)

(52) U.S. Cl.
CPC .......... *A61B 8/4209* (2013.01); *A61B 8/0825* (2013.01); *A61B 8/483* (2013.01); *A61B 8/403* (2013.01)

(58) Field of Classification Search
CPC ..... A61B 8/0825; A61B 8/403; A61B 8/4209; A61B 8/4461; A61B 8/483
See application file for complete search history.

(56) References Cited

U.S. PATENT DOCUMENTS

2016/0166217 A1 6/2016 Davis et al.
2016/0166234 A1* 6/2016 Zhang .................. A61B 8/4209
600/443

(Continued)

OTHER PUBLICATIONS

Office action dated Dec. 6, 2024 on U.S. Appl. No. 18/136,926.
Office action dated Mar. 24, 2025 on U.S. Appl. No. 18/136,926.

*Primary Examiner* — Brooke Lyn Klein
(74) *Attorney, Agent, or Firm* — Brunet & Co. Ltd.; Robert Brunet; Hans Koenig

(57) ABSTRACT

A whole breast 3D ultrasound imaging system involves a wearable adapter subassembly, a compression plate subassembly releasably mountable on the wearable adapter subassembly and a motor plate subassembly releasably mountable on the compression plate subassembly so that the compression plate subassembly is between the wearable adapter subassembly and the motor plate subassembly. The wearable adapter subassembly acts as a dam to contain ultrasound fluid around a subject's breast. The compression plate subassembly has an ultrasound compression plate in a frame, whereby the ultrasound compression plate is height adjustable. The motor plate subassembly has an ultrasound transducer and an actuator operatively coupled to the ultrasound transducer to translate the ultrasound transducer in a plane parallel to the ultrasound compression plate. The imaging system is cost-effective, portable and hands-free and can be used for bedside point-of-care imaging to acquire clear, sharp 3D ultrasound images of dense and/or small breasts.

16 Claims, 19 Drawing Sheets

(56) References Cited

U.S. PATENT DOCUMENTS

| | | | | |
|---|---|---|---|---|
| 2017/0311923 | A1 | 11/2017 | Saberi et al. | |
| 2019/0125304 | A1* | 5/2019 | Whisler | A61B 8/4494 |

* cited by examiner

WEARABLE 3D ULTRASOUND-BASED WHOLE BREAST IMAGING SYSTEM

CROSS-REFERENCE TO RELATED APPLICATIONS

This application is a continuation of U.S. Ser. No. 18/136,926 filed Apr. 20, 2023, which claims the benefit of U.S. Provisional Patent Application 63/335,857 filed Apr. 28, 2022, the entire contents of both of which are herein incorporated by reference.

FIELD

This application relates to medical devices and methods, in particular to a wearable whole breast three-dimensional (3D) ultrasound imaging system.

BACKGROUND

Breast cancer is the leading cause of cancer incidence and cancer-related deaths in women worldwide. Widely employed mammographic screening methods for breast cancer have improved treatment outcomes and reduced mortality in this population through the early detection of breast cancer. However, the diagnostic sensitivity for detecting small, early-stage breast cancer is significantly reduced in women with dense (small) breasts. Furthermore, mammographic density (MD) alone has been established as a strong, independent risk factor for developing invasive breast cancer, with a four to six times increased risk in women with dense breasts. The complex dynamic between risk factors such as age, body mass index (BMI), reproductive factors, hormonal status, menopausal status, and increased mammographic density over time may further increase the uncertainty of breast cancer detection at the time of imaging. These variable uncertainties may increase the number of false-positive findings, resulting in unnecessary breast biopsy procedures and interventions. Additionally, under current mammographic screening recommendations, the associated exposure due to ionizing radiation may not be ideal for screening younger, high-risk women with dense breasts. Due to these aforementioned challenges, there is still an urgent need for improved screening methods in the intermediate to high-risk women with dense breasts.

3D ultrasound (3D US) is one technique used for imaging whole breasts to screen for cancer. In some prior art approaches to 3D ultrasound, a subject is supine lying face up, and a mechanical arm holding an ultrasound transducer is deployed over the subject. The transducer is then swept across the surface of the breast. One issue with this approach is movement of the subject due to breathing causing blurry images and image artefacts. In another prior art approach, called the "pendulous" approach, a subject lies prone face down over a cavity in an imaging table with the breast hanging into the cavity. The cavity is filled with ultrasound transmission fluid, for example ultrasound gel or water, and an ultrasound transducer is manipulated over the exterior of the cavity from underneath the table. The image quality is not good in the pendulous approach, particularly for smaller, denser breasts.

Improving accessible, cost-effective methods for the early detection of breast cancer remains a challenge in development and clinical practice, particularly in the intermediate to high-risk population of women with dense breasts. Specifically, with supine detection systems, removing the need for medical cart-based systems and mechanical arms for automated scanning may provide a cost-effective, portable and hands-free whole-breast 3D ultrasound imaging technique. Furthermore, systems with the capability for bedside point-of-care (POC) imaging would be useful.

Thus, there remains a need for whole breast 3D ultrasound imaging systems, especially for dense breasts, which are cost-effective, portable and hands-free and can be used for bedside point-of-care imaging.

SUMMARY

A whole breast 3D ultrasound imaging system comprises: a wearable adapter subassembly comprising an annular wall for containing an ultrasound transmission fluid around a breast of a subject, the annular wall comprising a first edge configured to conform to a body surface around the breast of the subject to reduce leakage of the ultrasound fluid between the first edge and the body of the subject, and a second edge; a compression plate subassembly releasably mountable on the second edge of the wearable adapter subassembly, the compression plate subassembly comprising an ultrasound compression plate that is height adjustable relative to the wearable adapter subassembly; and, a motor plate subassembly releasably mountable on the wearable adapter subassembly, the motor plate subassembly comprising an ultrasound transducer movable on the motor plate subassembly in a plane parallel to the ultrasound compression plate.

In some embodiments, a whole breast 3D ultrasound imaging system comprises: a wearable adapter subassembly comprising an annular wall for containing an ultrasound transmission fluid around a breast of a subject, the annular wall comprising a first edge configured to conform to a body surface around the breast of the subject to reduce leakage of the ultrasound fluid between the first edge and the body of the subject, and a second edge; a compression plate subassembly releasably mountable on the second edge of the wearable adapter subassembly, the compression plate subassembly comprising a securement portion configured to be releasably secured to the second edge of the annular wall of the wearable adapter, and a frame with an ultrasound compression plate mounted to the frame, whereby the ultrasound compression plate is height adjustable relative to the securement portion; and, a motor plate subassembly releasably mountable on the compression plate subassembly so that the compression plate subassembly is between the wearable adapter subassembly and the motor plate subassembly, the motor plate subassembly comprising an ultrasound transducer movably mounted thereon, and an actuator operatively coupled to the ultrasound transducer to translate the ultrasound transducer in a plane parallel to the ultrasound compression plate.

The whole breast 3D ultrasound imaging system is cost-effective, portable and hands-free and can be used for bedside point-of-care imaging. The whole breast 3D ultrasound imaging system is particularly useful for acquiring clear, sharp 3D ultrasound images of dense and/or small breasts. The whole breast 3D ultrasound imaging system provides for a wearable device in which a conventional hand-held 3D ultrasound transducer or a motorized sweeping assembly with a 2D ultrasound transducer moves with the subject while the subject is breathing resulting in clearer 3D ultrasound images, while facilitating scanning with the ultrasound transducer over a surface of a conventional ultrasound compression plate. The imaging system is further provided with hardware and software to capture and store the relative 3D position and orientation of multiple 3D ultrasound images, or 2D ultrasound images in the case of a 2D ultrasound transducer on the motorized sweeping assembly, for reconstruction in a single volume for increased image size and/or resolution.

In some embodiments, the wearable adapter subassembly comprises a flexible gasket on the first edge to assist with conforming the first edge to the body surface of the subject. In some embodiments, the wearable adapter subassembly comprises a hinge permitting the annular wall to flex to assist with conforming the first edge to the body surface of the subject. In some embodiments, the wearable adapter subassembly further comprises a flexible membrane covering an open face thereof. The flexible membrane is preferably deformable by the breast when the breast is housed within the wearable adapter subassembly to prevent the breast from directly contacting the ultrasound transmission fluid within the wearable adapter subassembly, although a small amount of ultrasound fluid may be required to couple the subject to the flexible membrane. In some embodiments, the wearable adapter subassembly comprises a fastener for fastening the wearable adapter subassembly to the subject.

In some embodiments, the frame comprises mounting bolts secured thereon. In some embodiments, the mounting bolts engage the securement portion to connect the frame to the securement portion. In some embodiments, at least one of the mounting bolts is rotatable in a threaded aperture in the securement portion to cause the frame and the ultrasound compression plate to move relative to the securement portion when the securement portion is secured to the wearable adapter subassembly. In some embodiments, the securement portion comprises mounting screws that are threadingly mated with corresponding threaded mounting apertures in the second edge of the wearable adapter subassembly to releasably secure the compression plate subassembly to the wearable adapter subassembly.

In some embodiments, the motor plate subassembly is mountable on the frame and moves with the compression plate during height adjustment of the compression plate. In some embodiments, the motor plate subassembly is mountable on the compression plate subassembly with mounting pins inserted in locating apertures. In some embodiments, the frame comprises mounting pins and the motor plate subassembly comprises a mounting plate having locating apertures therein, the locating apertures aligning with the mounting pins so that the motor plate subassembly is mountable on the frame by insertion of the mounting pins into the locating apertures. In some embodiments, the mounting pins and the locating apertures are configured so that the motor plate subassembly can be rotated 90° and still be mountable on the mounting pins.

In some embodiments, the motor plate subassembly comprises a plurality of rails on which the ultrasound transducer is mountable. In some embodiments, the plurality of rails comprises one or more fixed rails. In some embodiments, the plurality of rails comprises one or more translatable rails. In some embodiments, the fixed rails comprise a first fixed rail orthogonal to a second fixed rail. In some embodiments, the translatable rails comprise a first translatable rail orthogonal to a second translatable rail. In some embodiments, one of the fixed rails extends in a craniocaudal direction and another of the fixed rails extends in a mediolateral direction, with respect to the breast when the imaging system is in use. In some embodiments, one of the translatable rails extends in a craniocaudal direction and another of the translatable rails extends in a mediolateral direction, with respect to the breast when the imaging system is in use. In some embodiments, the motor plate subassembly comprises a motor operatively connected to the one or more translatable rails, whereby operation of the motor causes translation of at least one of the one or more translatable rails. In some embodiments, the motor operatively connected to the one or more translatable rails through a timing belt (e.g., a chain or a strap) driven by a motor to translate the one or more translatable rails. However, other operative linkages such as gears may be used. In some embodiments, the motor plate subassembly comprises one or more quick-release mechanisms (e.g., spring-loaded pins, clamps, hooks and the like) to prevent or allow translation of the one or more translatable rails and/or rotation of the ultrasound transducer.

The plurality of rails allows a user to scan in two orthogonal directions without removing the entire motor plate subassembly during scanning. To save time and eliminate the need to remove and reposition the entire motor plate subassembly at 90 degrees for a second scan set, the timing belt may be situated to encircle a perimeter of the wearable adapter subassembly. Incorporation of the one or more quick-release mechanisms permits changing orientation of and direction of travel of the ultrasound transducer. In some embodiments, the ultrasound transducer is rotatable to change the orientation of the ultrasound transducer between the craniocaudal direction and the mediolateral direction. In some embodiments, the ultrasound transducer is translatable in the craniocaudal and mediolateral directions by virtue of the being mountable on the translatable rails. Selective engagement of the one or more quick-release mechanisms determines the direction in which the translatable rails, and therefore the ultrasound transducer, moves. Thus, the motor plate subassembly only needs to be dismounted between patients who require a different wearable adapter subassembly to accommodate varying patient breast geometry (e.g., cup sizes).

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1:
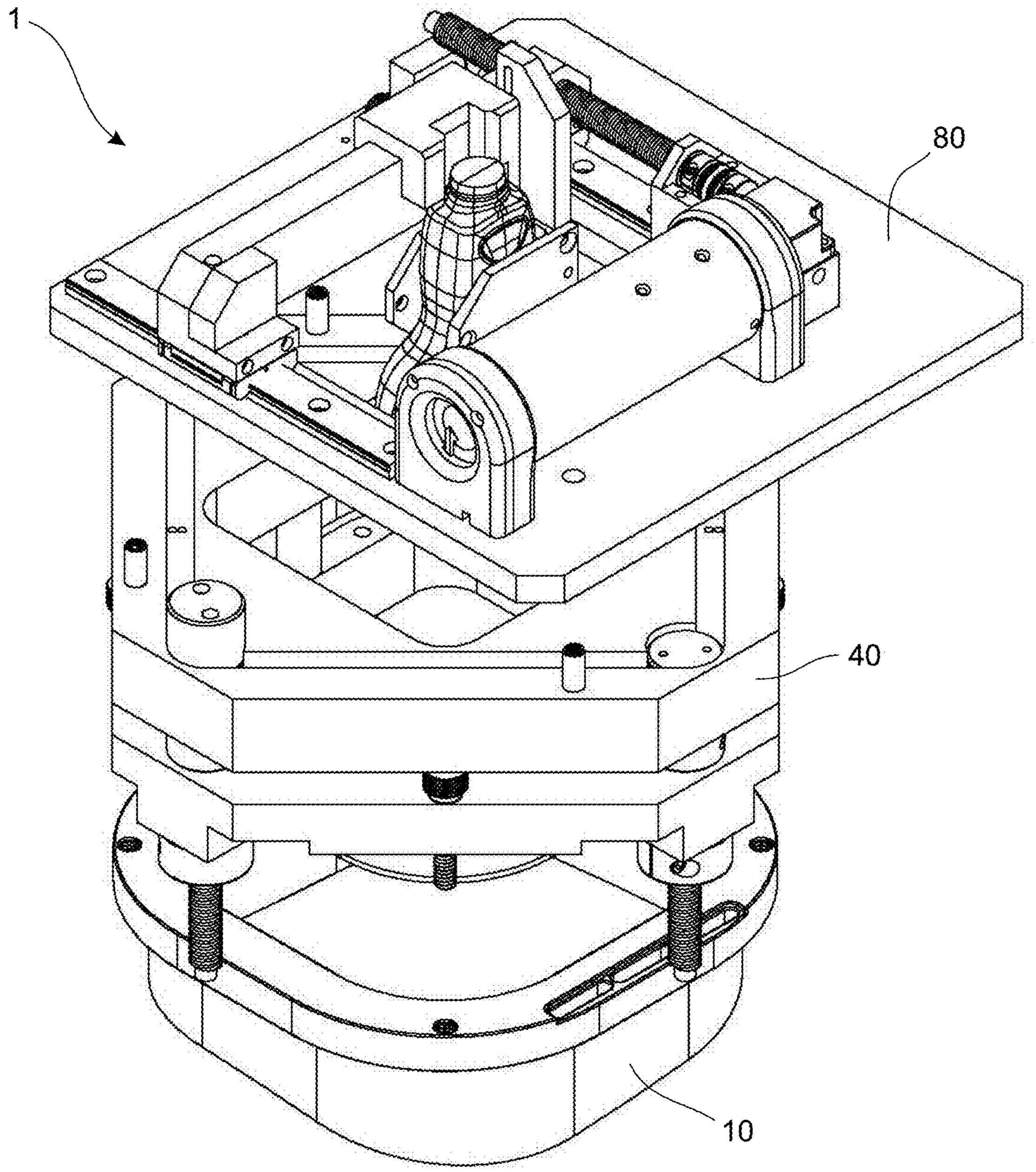
FIG. 1 depicts an exploded view of a whole breast 3D ultrasound imaging system.

With reference to the Figures, a whole breast 3D ultrasound imaging system 1 comprises three subassemblies including a wearable adapter subassembly 10, a compression plate subassembly 40 and a motor plate subassembly 80 releasably stackable on each other with the compression plate subassembly 40 between the wearable adapter subassembly 10 and the motor plate subassembly 80. The ultrasound imaging system 1 is particularly useful for capturing images of a breast of a supine subject 100 where the wearable adapter subassembly 10 is in contact with the subject and the compression plate subassembly 40 and the motor plate subassembly 80 are stacked on the wearable adapter subassembly 10 with the wearable adapter subassembly 10 at a bottom of the stack and the motor plate subassembly 80 at a top of the stack.

Figure 2A:
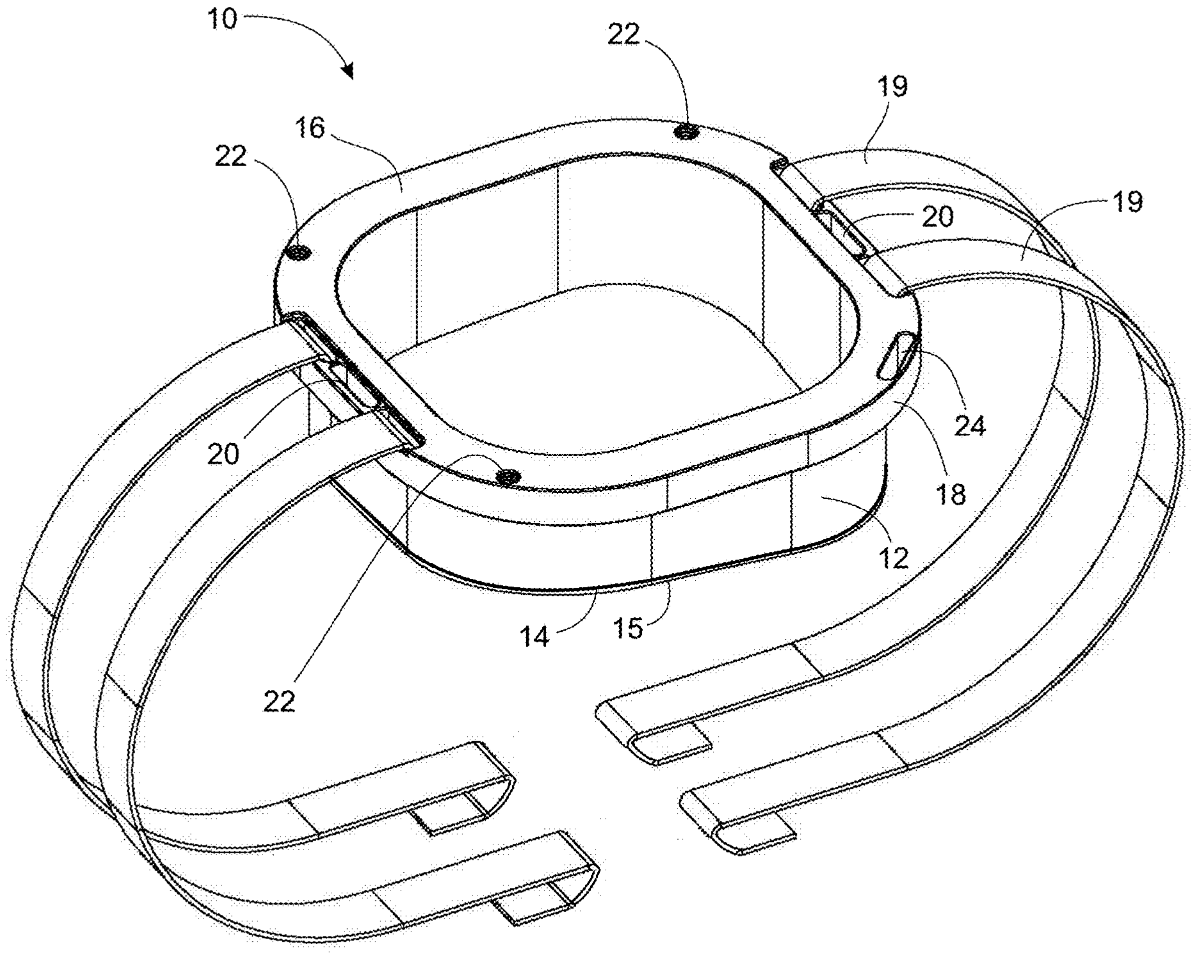
FIG. 2A depicts a rigid wearable adapter subassembly of the imaging system of FIG. 1.

With reference to FIG. 2A, the wearable adapter subassembly 10 comprises an annular wall 12 forming a hollow ring having opposed lower and upper open faces, the annular wall 12 defining a volume for containing ultrasound transmission fluid (e.g., ultrasound gel) around a breast of a subject during operation of the ultrasound imaging system 1. During operation of the ultrasound imaging system 1, the breast of the subjects is housed within the annular wall 12. Thus, the wearable adapter 10 acts as a dam for containing ultrasound transmission fluid around the breast of the subject. The annular wall 12 comprises a lower edge 14 and an upper edge 16, the upper edge 16 having a lip 18 that overhangs the annular wall 12 toward an outside of the wearable adapter subassembly 10. The lower edge 14 is configured to conform to a body surface around the breast of the subject to reduce leakage of the ultrasound transmission fluid between the lower edge 14 and the body of the subject 100. The lower edge 14 is thus shaped to follow contours of the subject's body in a region around the subject's breast. To facilitate sealing the lower edge 14 to the subject's body, the lower edge 14 is provided with a compressible gasket 15 (e.g., silicone tubing or other elastomeric material), which forms a better seal with skin.

The upper edge 16 is flat and has features for mounting additional structures thereon. The lip 18 of the upper edge 16 comprises slots 20 on opposite sides of the wearable adapter subassembly 10, in which adjustable straps 19 are accommodated to be able to strap the wearable adapter subassembly 10 to the subject 100. Being able to strap the wearable adapter subassembly 10 to the subjects makes the ultrasound imaging system 1 wearable and further helps seal the wearable adapter subassembly 10 to the skin of the subject 100. The upper edge 16 further comprises mounting apertures 22 therein that align with and receive mounting screws 41 on the compression plate subassembly 40 for securely but releasably mounting the compression plate subassembly 40 on the wearable adapter subassembly 10. The mounting apertures 22 are threaded and the mounting screws on the compression plate subassembly 40 are matingly threaded to be able to secure the compression plate subassembly 40 on the wearable adapter subassembly 10. The upper edge 16 further comprises an index slot 24 that helps align the mounting apertures 22 of the wearable adapter subassembly 10 with the mounting screws 41 of the compression plate subassembly 40 to be able to mount the compression plate subassembly 40 on the wearable adapter subassembly 10 in the proper orientation. The index slot 24 can also accommodate the adjustable straps 19 to further facilitate strapping the wearable adapter subassembly 10 to the subject 100.

In some embodiments, the wearable adapter subassembly 10 further comprises a flexible membrane covering the lower open face, which is deformable by the breast when the breast is housed within the annular wall 12. The membrane conforms to the breast to prevent the breast from directly contacting the ultrasound transmission fluid, which simplifies clean-up and permits re-use of most of the ultrasound transmission fluid.

Figure 8A:
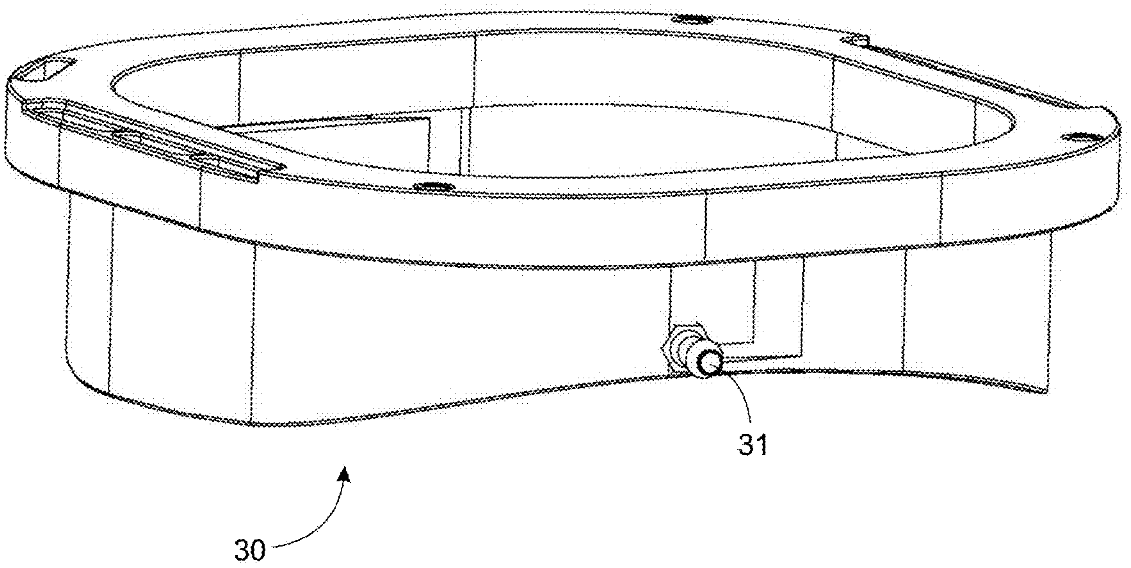
FIG. 8A depicts a rigid wearable adapter subassembly design for the imaging system.
Figure 8B:
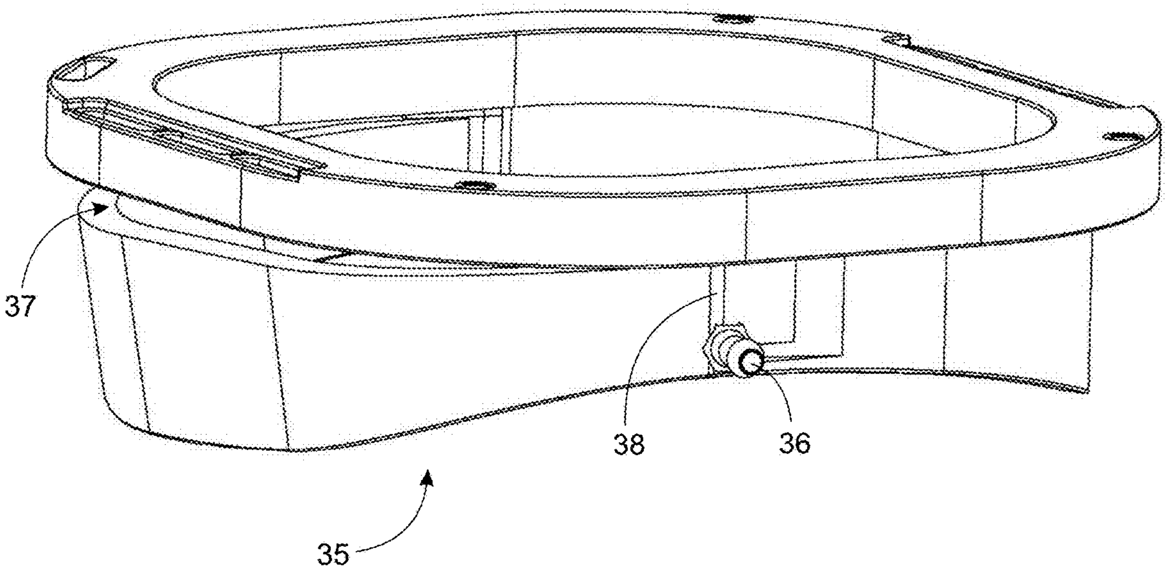
FIG. 8B depicts a flexible wearable adapter subassembly design for the imaging system.

With reference to FIG. 8A and FIG. 8B, variations of the wearable adapter subassembly are illustrated. In one variation, the wearable adapter subassembly is a rigid wearable adapter subassembly 30 having a fluid port 31 in the annular wall. The fluid port 31 permits draining the ultrasound transmission fluid in a controlled manner after the ultrasound imaging operation is completed. In another variation, the wearable adapter subassembly is a flexible wearable adapter subassembly 35 having a fluid port 36 in the annular wall and both a transverse cut 37 proximate the upper edge below the lip running about halfway along the annular wall and a longitudinal cut 38 running down the annular wall from an end of the transverse cut 37 to the fluid port 36 to form a flexible hinge that permits the annular wall to flex at the fluid port 36. The flexible hinge facilitates conforming the lower edge of the flexible wearable adapter subassembly 35 to the body surface of the subject. The fluid port 36 may be used to drain unwanted ultrasound transmission fluid from the wearable adapter subassembly 35.

Figure 2B:
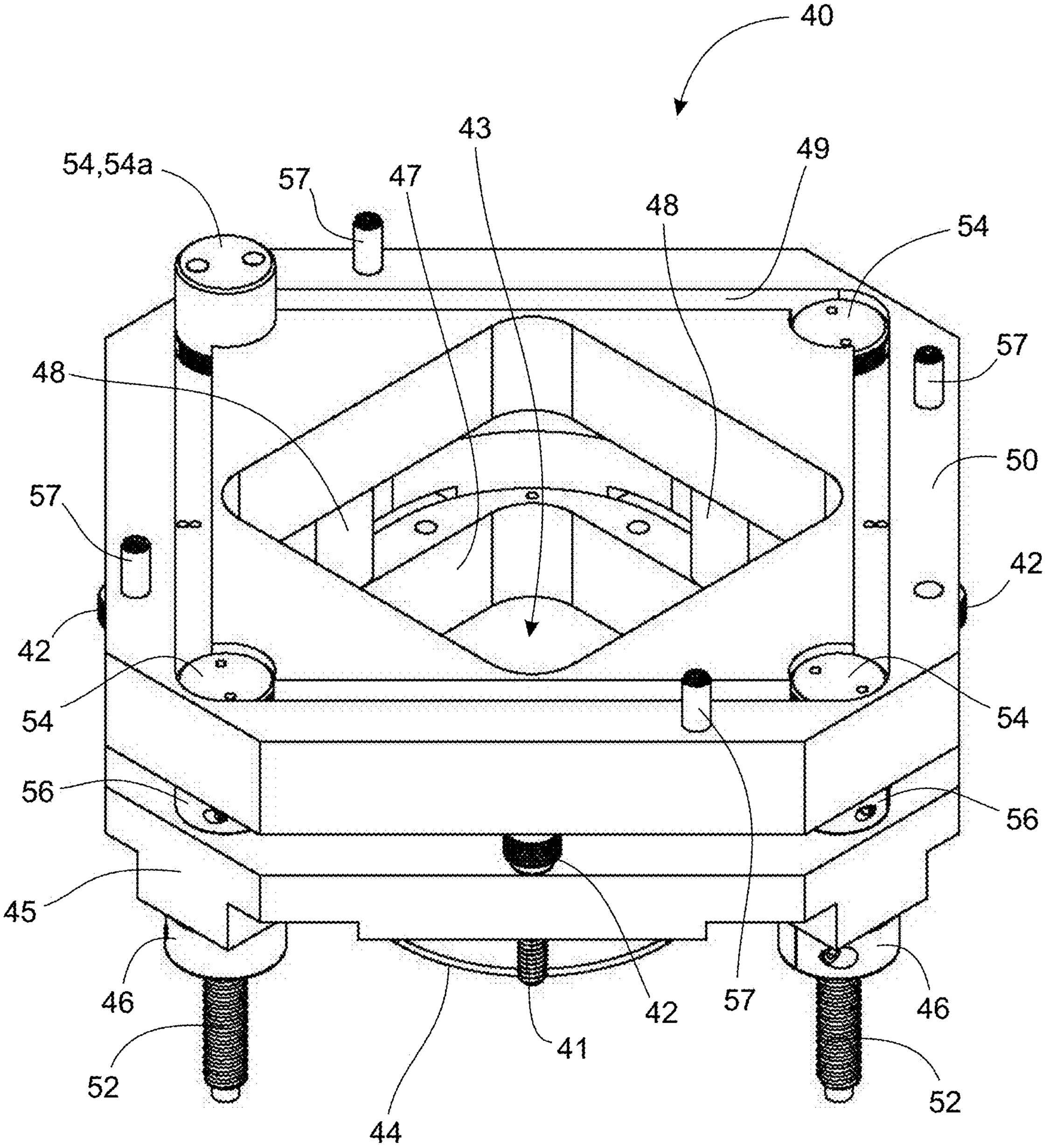
FIG. 2B depicts a perspective view of a compression plate subassembly of the imaging system of FIG. 1.

With reference to FIG. 2B, the compression plate subassembly 40 comprises a securement portion 45 and an upper frame 50 height adjustably mounted on the securement portion 45 so that the securement portion 45 is between the wearable adapter subassembly 10 and the upper frame 50 when the compression plate subassembly 40 is mounted on the wearable adapter subassembly 10. The securement portion 45 is releasably mounted on and secured to the upper edge 16 of the wearable adapter subassembly 10 by the mounting screws 41 (only one shown) mounted in the securement portion 45 and insertable into the mounting apertures 22 in the upper edge 16 of the wearable adapter subassembly 10. To releasably secure the securement portion 45, and therefore the entire compression plate subassembly 40, to the wearable adapter subassembly 10, the mounting screws 41 are threadingly mated with the corresponding threaded mounting apertures 22 and can be screwed into the threaded mounting apertures 22 by operation of knurled knobs 42 attached to the mounting screws 41. The securement portion 45 comprises connected frame elements that bound an opening 43 through which an ultrasound compression plate 44 can move. The compression plate 44 is rigidly connected ultimately to the upper frame 50, the upper frame 50 being the same general size and shape as the securement portion 45 and situated above the securement portion 45. To connect the ultrasound compression plate 44 to the upper frame 50, the upper frame 50 is rigidly connected to mounting posts 48, which extend downwardly to, and are rigidly connected to, a window frame 47. The window frame 47 is a square frame with rounded corners, the window frame 47 being smaller than the upper frame 50. The ultrasound compression plate 44 is rigidly connected to the window frame 47 below the window frame 47. The ultrasound compression plate 44 and the window frame 47 are sized to fit within the confines of the annular wall 12 of the wearable adapter subassembly 10. The compression plate 44, window frame 47, mounting posts 48 and upper frame 50 form a single rigid part. The window frame 47 forms a seal with an inside surface of the annular wall 12 by minimizing, without closing, an air gap between the inside surface of the annular wall 12 and an outside surface of the window frame 47 to inhibit leakage of the ultrasound transmission fluid between the wearable adapter subassembly 10 and the compression plate subassembly 40 when the compression plate 44 presses down toward or on the breast of the subject 100. The small air gap between annular wall 12 and the window frame 47 allows air bubbles to escape from the wearable adapter subassembly 10 but prevents the ultrasound transmission fluid from escaping due to large friction forces created from the relatively large viscosity of the ultrasound transmission fluid being forced through a small air gap compared to air which can flow freely through the small air gap.

The ultrasound compression plate 44, for example a TPX plate (made from a 4-methylpentene-1-based polyolefin plastic), is ultimately mounted to and underneath the upper frame 50. The ultrasound compression plate 44 together with the window frame 47 move with the upper frame 50 during height adjustment of the upper frame 50. Height adjustment of the upper frame 50 relative to the securement portion 45 is accomplished with threaded mounting bolts 52. The threaded mounting bolts 52 are mounted in bores through the upper frame 50, upper ends of the mounting bolts 52 having grooved bolt heads 54 seated in the bores. The mounting bolts 52 extend out a bottom of the upper frame 50 through corresponding threaded holes in the securement portion 45 and through lockable bosses 46 on a lower face of the securement portion 45. The lockable bosses 46 can be loosened to permit height adjustability of the upper frame 50 or tightened to secure the upper frame 50 in position relative to the securement portion 45. Mounted on the mounting bolts 52 between the securement portion 45 and the upper frame 50 are lockable stops 56 to hold the mounting bolts 52 in place in the upper frame 50. One of the bolt heads 54 is an adjustment knob 54*a*, whereby all of the bolt heads 54, are mechanically linked to each other via a timing belt (not shown) located in a groove 49 in an inner face of the upper frame 50, the timing belt operatively linking the grooved bolt heads 54, including the knob 54*a*. When the lockable bosses 46 are loosened, rotation of the adjustment knob 54*a* causes the mounting bolt (not shown) and all of the other mounting bolts 52 connected to the adjustment knob 54*a* via the timing belt to turn in the corresponding threaded holes thereby causing the upper frame 50 to move up and down relative to the securement portion 45. In use, height adjustment of the upper frame 50 is adjusted so that the compression plate 44 compresses the ultrasound transmission fluid slightly in order to cause the transmission fluid to flow and fill any voids around the breast, thereby ensuring that the compression plate 44 continuously engages either the breast or the ultrasound transmission fluid. A flat scanning surface in "sonic engagement" with the breast is thereby achieved.

The compression plate subassembly 40 further comprises mounting pins 57 extending from an upper surface of the upper frame 50. The mounting pins 57 permit releasably mounting of the motor plate subassembly 80 on the compression plate subassembly 40.

Figure 2C:
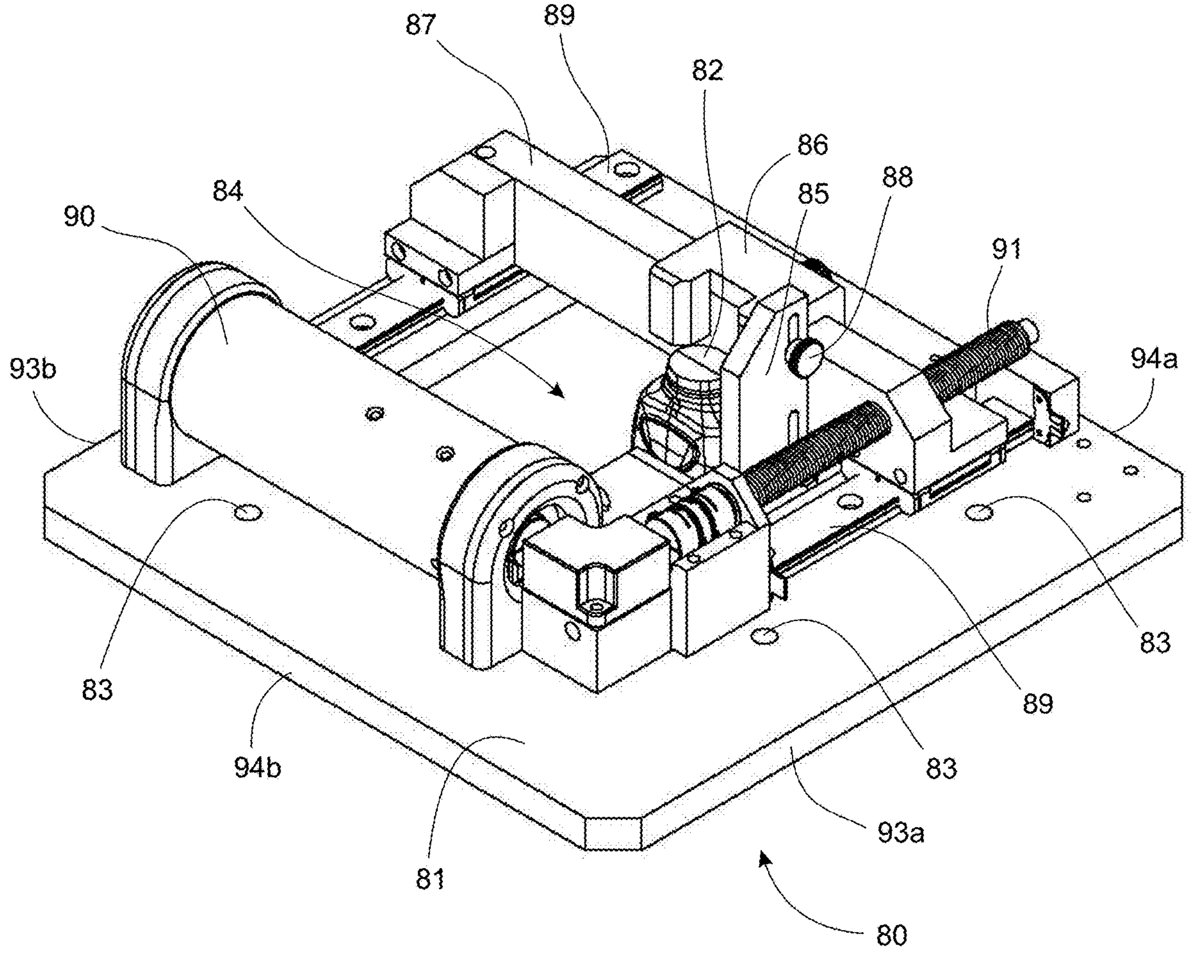
FIG. 2C depicts a perspective view of a motor plate subassembly of the imaging system of FIG. 1.

With reference to FIG. 2C, the motor plate subassembly 80 comprises a mounting plate 81 on which an ultrasound transducer 82 is mounted. The motor plate subassembly 80 is releasably mountable on the compression plate subassembly 40 by virtue of locating apertures 83 (only three of four shown) in the mounting plate 81, which are positioned to align with at least two of the mounting pins 57 on the frame 50 of the compression plate subassembly 40. The motor plate subassembly 80 can be simply placed on and lifted off the mounting pins 57 to permit changing the orientation of the the motor plate subassembly 80 by 90° or 180°.

The mounting plate 81 comprises a large through-aperture 84 within which the ultrasound transducer 82 is situated and through which the ultrasound transducer 82 extends to contact the ultrasound compression plate 44 when the motor plate subassembly 80 is mounted on the compression plate subassembly 40. The ultrasound transducer 82 is mounted on a mounting bracket 85, which is mounted on a cradle 86. The cradle 86 is slidingly mounted on a carriage 87. The carriage 87 is slidingly mounted on rails 89, the rails 89 fixed to an upper surface of the mounting plate 81. The carriage 87 is operatively connected to an actuator comprising a motor 90 and a threaded drive rod 91 extending through a matingly threaded through-aperture in the carriage 87. The drive rod 91 is rotatably connected to a drive shaft of the motor 90 through appropriate gears or other linkages. Operation of the motor 90 rotates the threaded drive rod 91 in the matingly threaded through-aperture of the carriage 87 thereby driving the carriage 87 linearly along the rails 89 between opposed sides 94*a* and 94*b* of the motor plate subassembly 80. The cradle 86 is manually slidable linearly on the carriage 87 between opposed sides 93*a* and 93*b* of the motor plate subassembly 80. Thus, linear motion of the carriage 87 on the rails 89 is perpendicular to linear motion of the cradle 86 on the carriage 87.

Therefore, the ultrasound transducer 82 can be driven automatically by the motor to perform a sweep along a first sweep axis, and can be moved manually transversely to the first sweep axis so that the ultrasound transducer 82 can be automatically driven along a second sweep axis parallel to the first sweep axis in order to image more of the breast. Thus, the motor 90 is used to sweep the ultrasound transducer 82 linearly across the the compression plate 44 in a direction perpendicular to a long dimension of the ultrasound transducer 82 and acquire a first 3D image that is rectangular in plan view. To acquire an image of a larger area, the ultrasound transducer 82 is manually re-positioned laterally on the carriage 87 to acquire a second 3D image, and the second image can be stitched together with the first image.

The ultrasound transducer 82 is mounted on the mounting bracket 85 by a height adjusting fitting 88 comprising a tightenable bolt disposed through a slot in the mounting bracket 85. Loosening the bolt permits the ultrasound transducer 82 to be raised and lowered relative to the mounting plate 81. While this could be useful, it is a particular advantage of the ultrasound imaging system 1 that a height of the ultrasound transducer 82 itself does not need to be adjusted to contact the compression plate 44 during operation of the ultrasound imaging system 1 because the entire motor plate subassembly 80 moves up and down in tandem with the compression plate 44 by virtue of being mounted on the upper frame 50 of the compression plate subassembly 40. The height adjustable upper frame 50 has a structurally defined depth between the compression plate 44 and the upper surface of the upper frame 50 so that, when the ultrasound transducer 82 is mounted on the cradle 86, the ultrasound transducer 82 engages the surface of the compression plate 44 and is at 90° (i.e., perpendicular) to the compression plate 44.

The ultrasound imaging system 1 has a number of advantages arising from the system's modularity and portability.

Figure 3A:
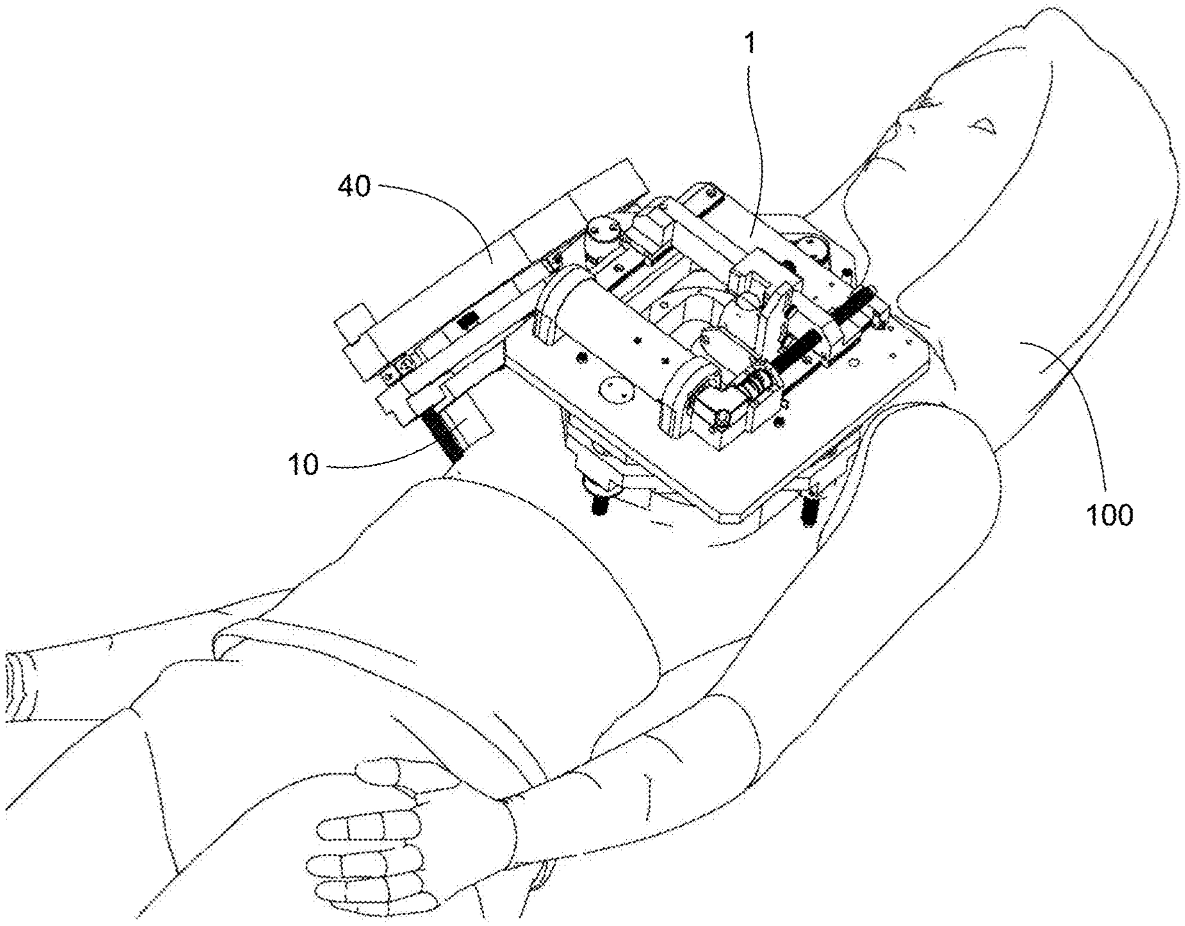
FIG. 3A depicts a subject having the imaging system of FIG. 1 mounted on the subject's left breast, and the compression plate subassembly of FIG. 2B with the wearable adapter subassembly of FIG. 2A mounted on the subject's right breast.

With reference to FIG. 3A, the subject 100 can wear on one breast (e.g., the right breast), the wearable adapter assembly 10 with the compression plate subassembly 40 secured thereon at the same time as wearing the entire ultrasound imaging system 1 on the other breast (e.g., the left breast). After finishing ultrasound imaging on one breast, the motor plate assembly can be quickly lifted off the compression plate subassembly 40 over that breast and placed on the compression plate subassembly 40 over the other breast, thereby speeding up overall workflow when imaging two breasts.

Figure 3B:
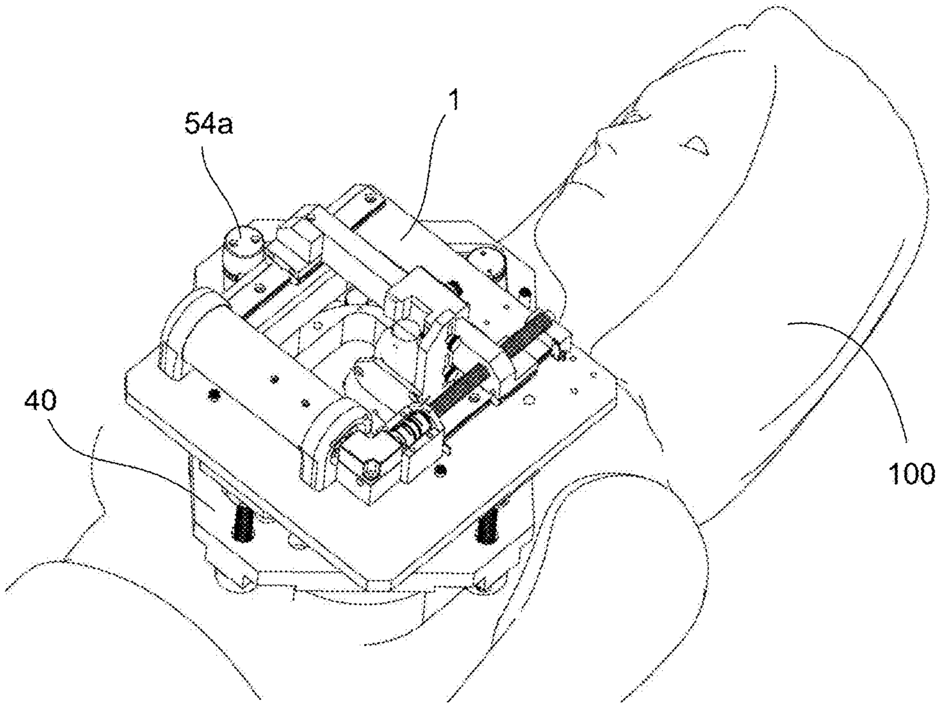
FIG. 3B depicts the imaging system of FIG. 1 mounted on the subject's left breast with the compression plate subassembly in an up configuration.
Figure 3C:
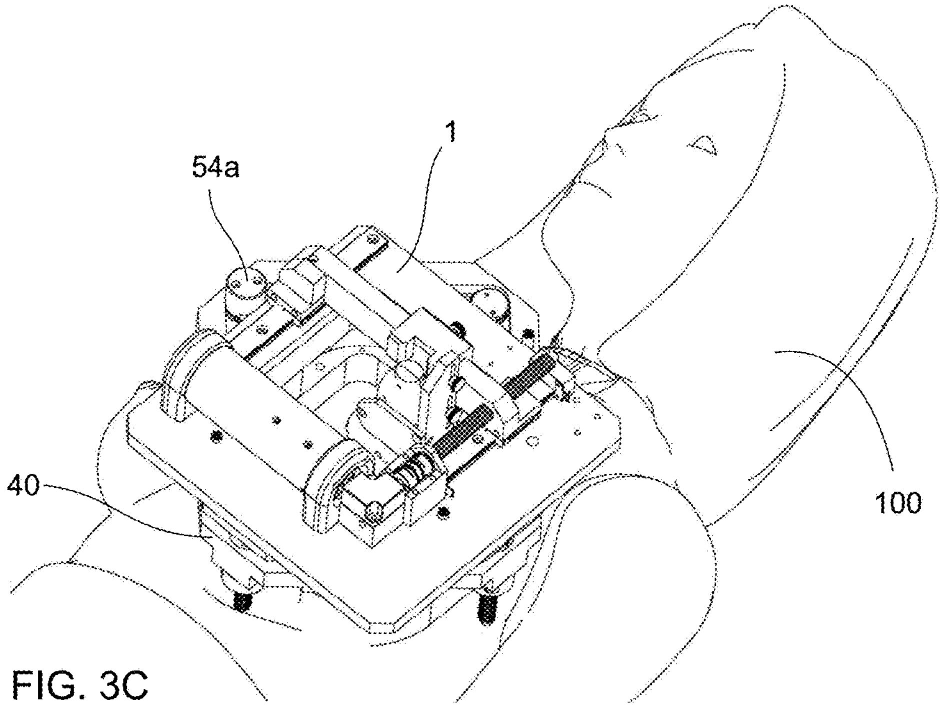
FIG. 3C depicts the imaging system of FIG. 1 mounted on the subject's left breast with the compression plate subassembly in a down configuration.
Figure 4A:
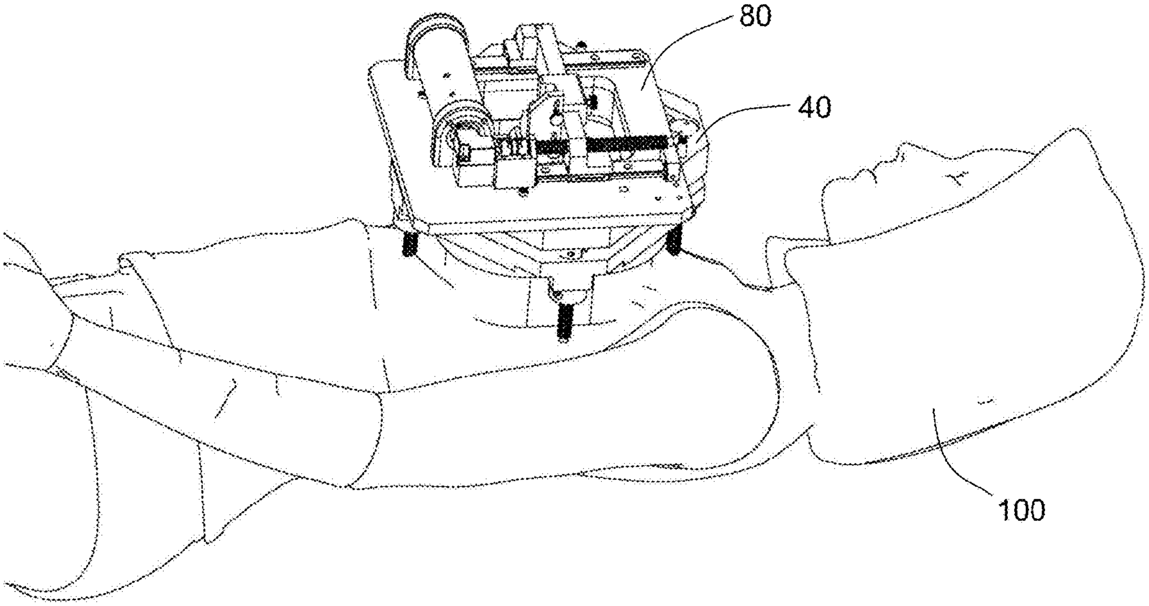
FIG. 4A depicts a subject having the imaging system of FIG. 1 mounted on the subject's left breast with the motor plate subassembly oriented as shown in FIG. 3B.
Figure 4B:
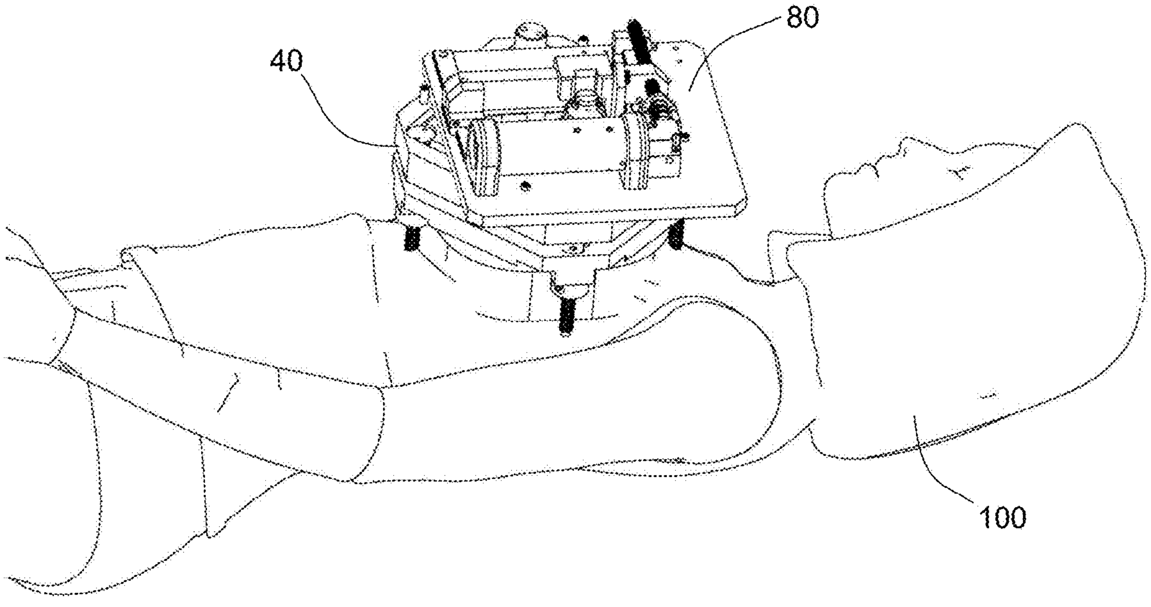
FIG. 4B depicts a similar view as FIG. 4A except that the motor plate subassembly is oriented at 90° to the orientation shown in FIG. 4A.
Figure 5A:
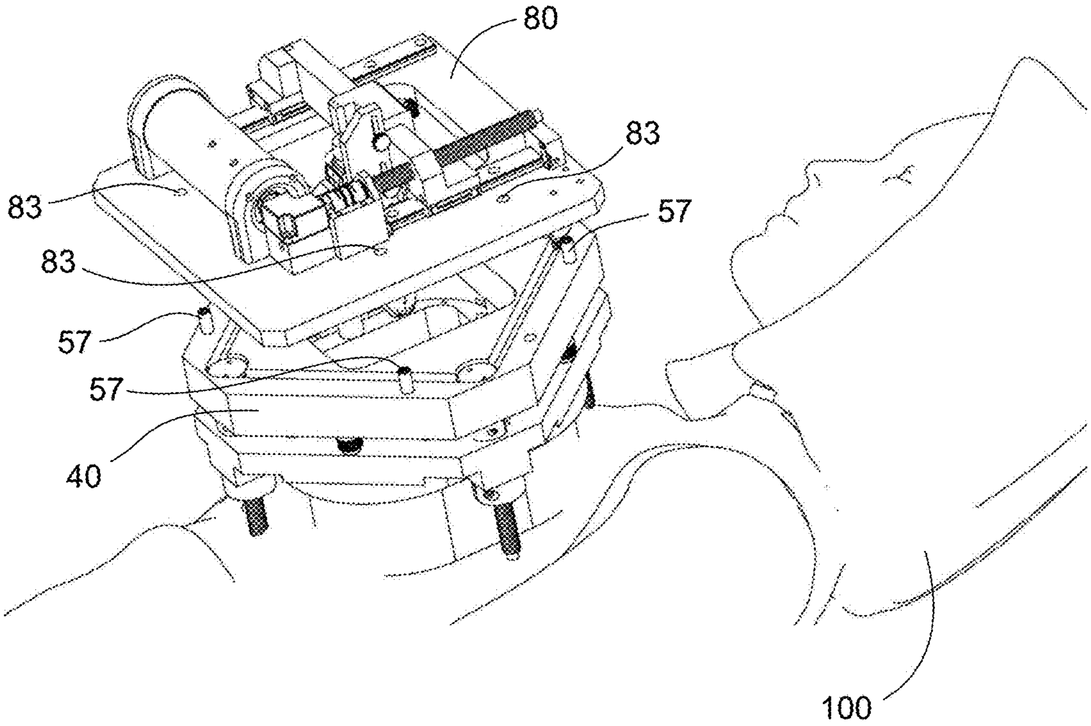
FIG. 5A depicts the motor plate and compression plate subassemblies showing pins and matching apertures for orienting the motor plate subassembly as shown in FIG. 4A.
Figure 5B:
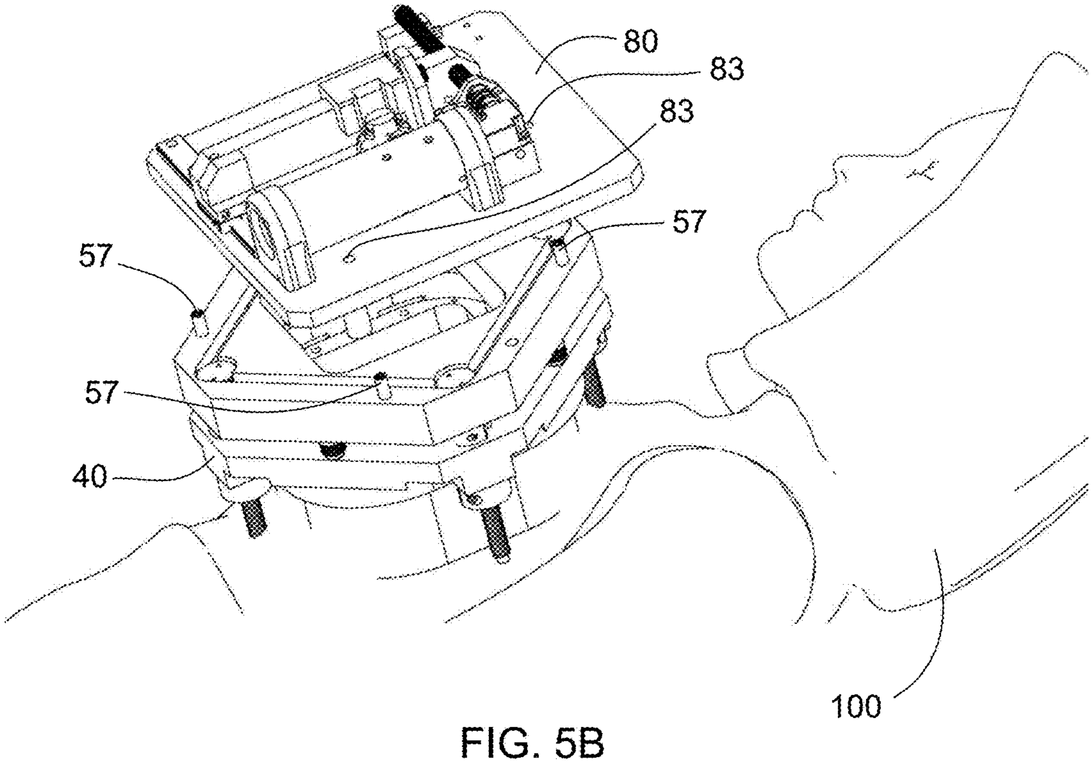
FIG. 5B depicts the motor plate and compression plate subassemblies showing pins and matching apertures for orienting the motor plate subassembly as shown in FIG. 4B.

With reference to FIG. 3B and FIG. 3C, the height adjustability of the upper frame 50 of the compression plate subassembly 40 between a raised position (FIG. 3B) and a lowered position (FIG. 3C) permits accommodating different breast sizes and fine tuning the position of the compression plate 44 without needing to do anything except turn the adjustment knob 54*a* and preferably the lock the lockable bosses 46 once the desired position of the compression plate 44 is attained. For a portable system, such a feature avoids time-consuming reconfiguration of the components.

With reference to FIG. 4A, FIG. 4B, FIG. 5A and FIG. 5B, the orientation, in plan view, of the motor plate subassembly 80 on the compression plate subassembly 40 can be changed quickly and simply by just lifting the motor plate subassembly 80 off the compression plate subassembly 40, turning the motor plate subassembly 80 90° and setting the motor plate subassembly 80 back on the compression plate subassembly 40 as permitted by the modular design of the ultrasound imaging system 1 and the design of the locating apertures 83 and the mounting pins 57. Being able to change the orientation of the motor plate subassembly 80 on the compression plate subassembly 40 by 90° permits sweeping the ultrasound transducer 82 in a perpendicular direction. Thus, scans of a target volume can be taken in a first direction (e.g., head to toe direction), then, following angular re-positioning of the motor plate subassembly 80, in a second direction (e.g., left to right). Further, because the motor plate subassembly 80 is separable from the compression plate subassembly 40, the ultrasound transducer 82 can be positioned at any desired angle relative to compression plate subassembly 40 by providing a suitably indexable structure. For example, in an alternative embodiment, the mounting pins 57 can be replaced by an arcuate track that allows the motor plate subassembly 80 to be rotated (as seen in plan view) relative to the compression plate subassembly 57 and locked at any desired angle relative to the compression plate subassembly 57.

Figure 6A:
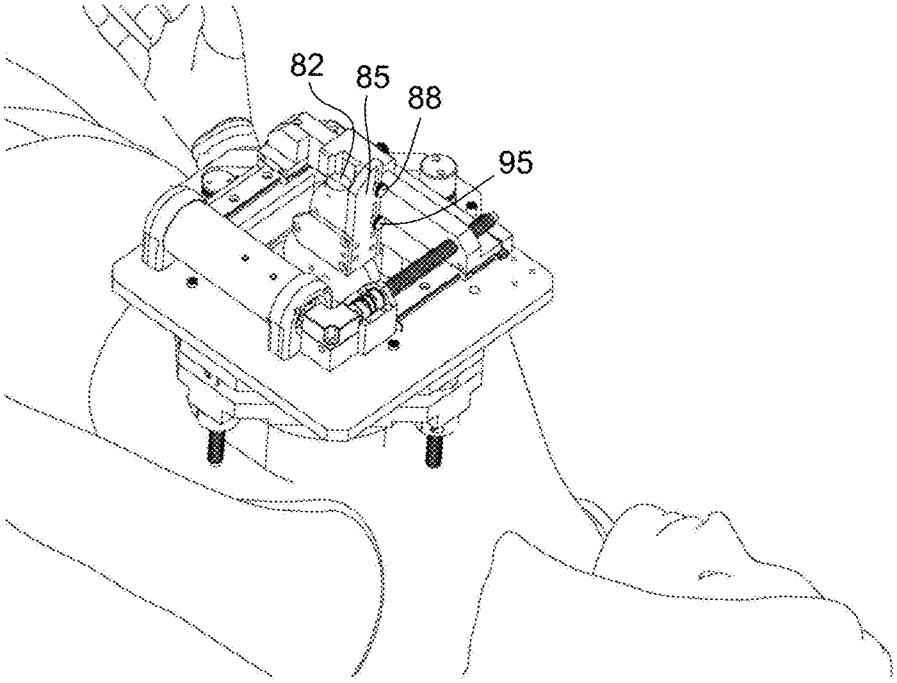
FIG. 6A depicts the imaging system with an ultrasound transducer configured in a non-tilted position.
Figure 6B:
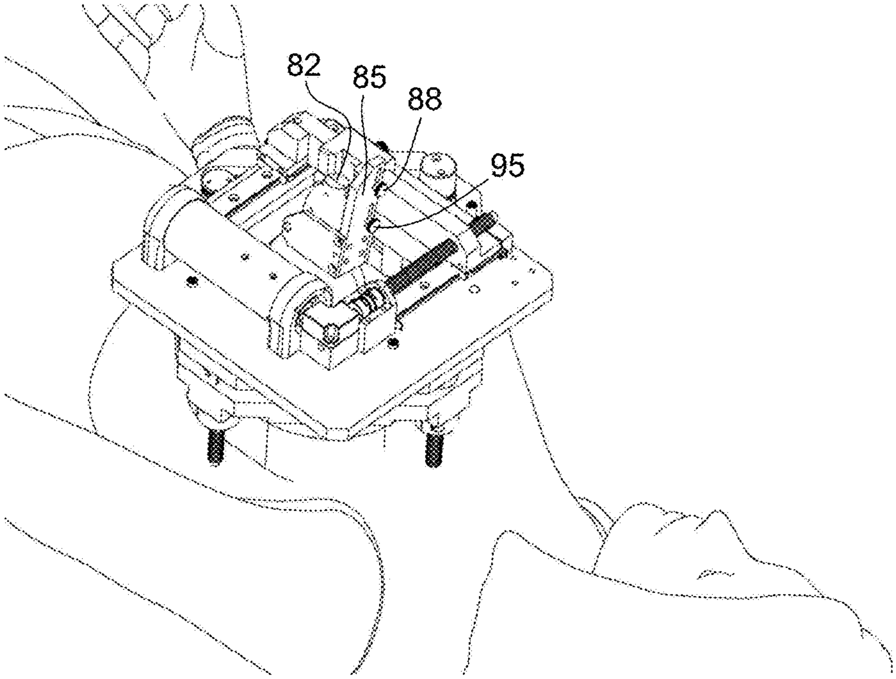
FIG. 6B depicts the imaging system with an ultrasound transducer configured in a tilted position.

With reference to FIG. 6A and FIG. 6B, the ultrasound transducer 82 can also be tilted from an orientation where a longitudinal axis of the ultrasound transducer 82 is in a vertical orientation (FIG. 6A) into an orientation where the longitudinal axis of the ultrasound transducer 82 is in a non-vertical orientation (FIG. 6B). By loosening the tightenable bolt of the height adjusting fitting 88 and loosening a tightenable bolt of a tilt adjusting fitting 95, the mounting bracket 85, and the ultrasound transducer 82 mounted thereon, can be tilted with a bottom thereof moving up out of the plane of the sheet as illustrated in FIG. 6B. Once the desired tilt is achieved, the two tightenable bolts are re-tightened.

With reference to FIG. 7A, FIG. 7B, FIG. 7C and FIG. 7D, the ultrasound imaging system 1 may be used to acquire 3D images or a series of 3D images in the following manner.

The wearable adapter assembly 10 is strapped to the subject 100 over one of the breasts. Once the straps are in place, and the wearable adapter assembly 10 is secure, a sufficient amount of ultrasound transmission fluid is poured into the volume defined by the annular wall 12 for containing the ultrasound transmission fluid to cover the whole breast and the surrounding volume.

The compression plate assembly 40 is then placed on top of the wearable adapter assembly 10 is and secured in place using the mounting screws 41. The adjustment knob 54*a* is then turned to lower the frame 50 of the compression plate assembly 40 until the breast is stabilized and the ultrasound transmission fluid is occupying the volume around the breast. A sufficient amount of ultrasound transmission fluid is added on top of the compression plate 44 so that the ultrasound transducer 82 is sonically coupled to both the subject 100 and the compression plate 44.

Figure 7A:
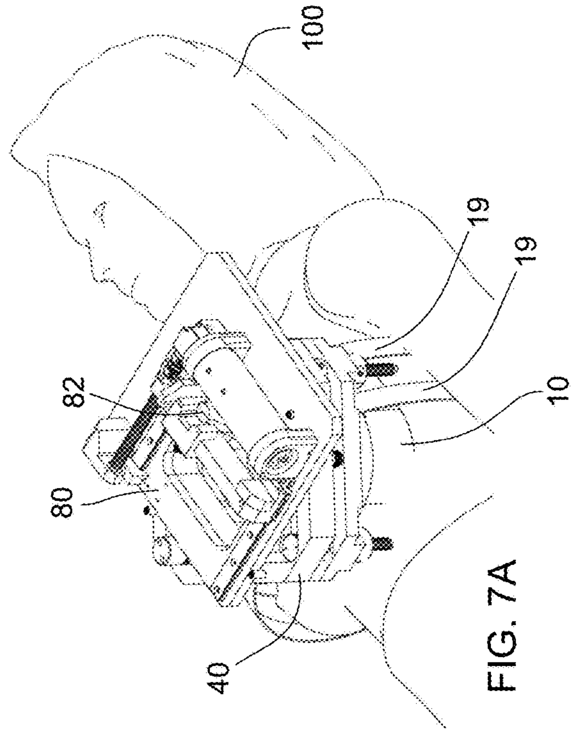
FIG. 7A, FIG. 7B, FIG. 7C and FIG. 7D illustrate four different positions of an ultrasound transducer on the motor plate subassembly when the imaging system of FIG. 1 is used to acquire ultrasound images.
Figure 7B:
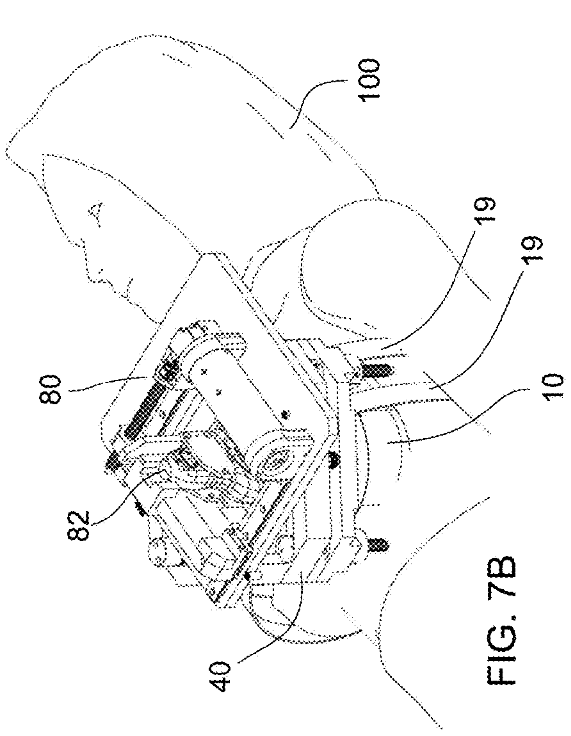
Figure 7C:
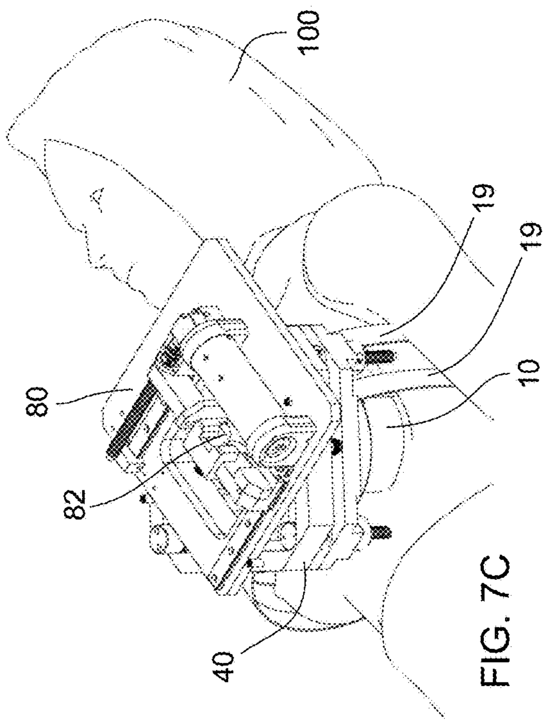
Figure 7D:
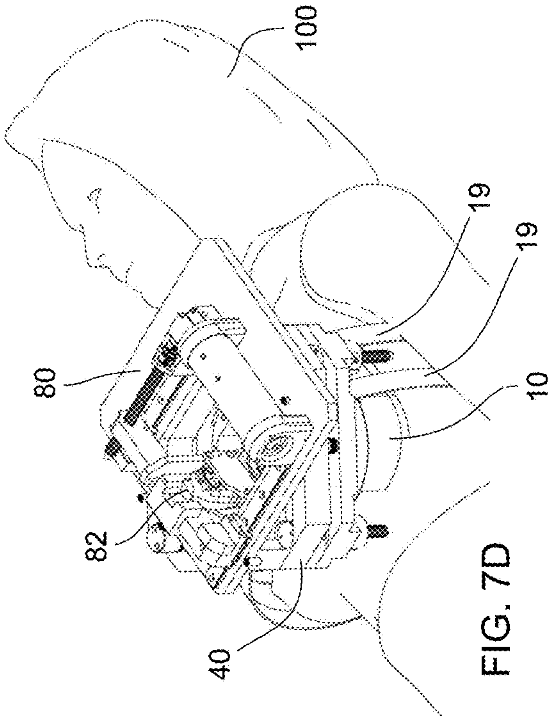

The motor plate subassembly 80 is placed on the compression plate subassembly 40 in one of the two possible orientations, for example the orientation shown in FIG. 7A. The cradle 86 with the ultrasound transducer 82 mounted thereon is manually moved along the carriage 87 to one of the fixed locations, for example the fixed location in FIG. 7A, so that the images overlap in the same volume. The actuator is actuated, for example from a computer, so that the motor 90 drives the carriage 87 linearly along the rails 89 until the ultrasound transducer 82 reaches the position shown in FIG. 7B to create a 3D ultrasound image of the scanned volume. Additional 3D images are then acquired to increase the image volume by driving the carriage 87 in reverse and then manually relocating the cradle 86, and the ultrasound transducer 82 mounted thereon, to another fixed location as shown in FIG. 7C. The carriage 87 is then driven linearly along the rails 89 until the ultrasound transducer 82 reaches the position shown in FIG. 7D to create another 3D ultrasound image. Alternatively, or additionally, image resolution can be improved by repositioning the motor plate subassembly to the other of the two orientations at 90° to the first, and then acquire images in a manner where the images acquired at both orientations overlap each other completely.

Figure 9:
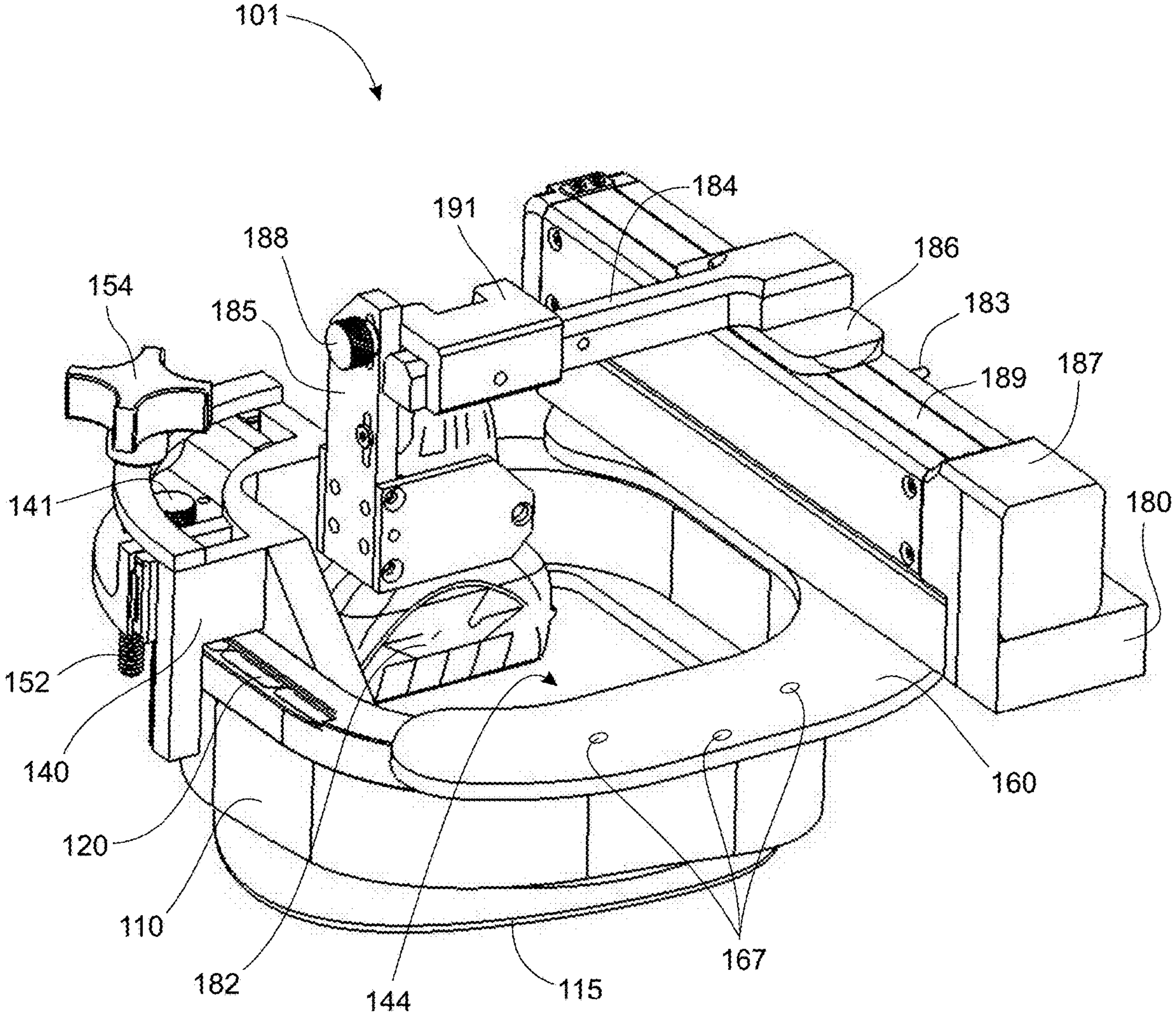
FIG. 9 depicts another embodiment of a whole breast 3D ultrasound imaging system.
Figure 10A:
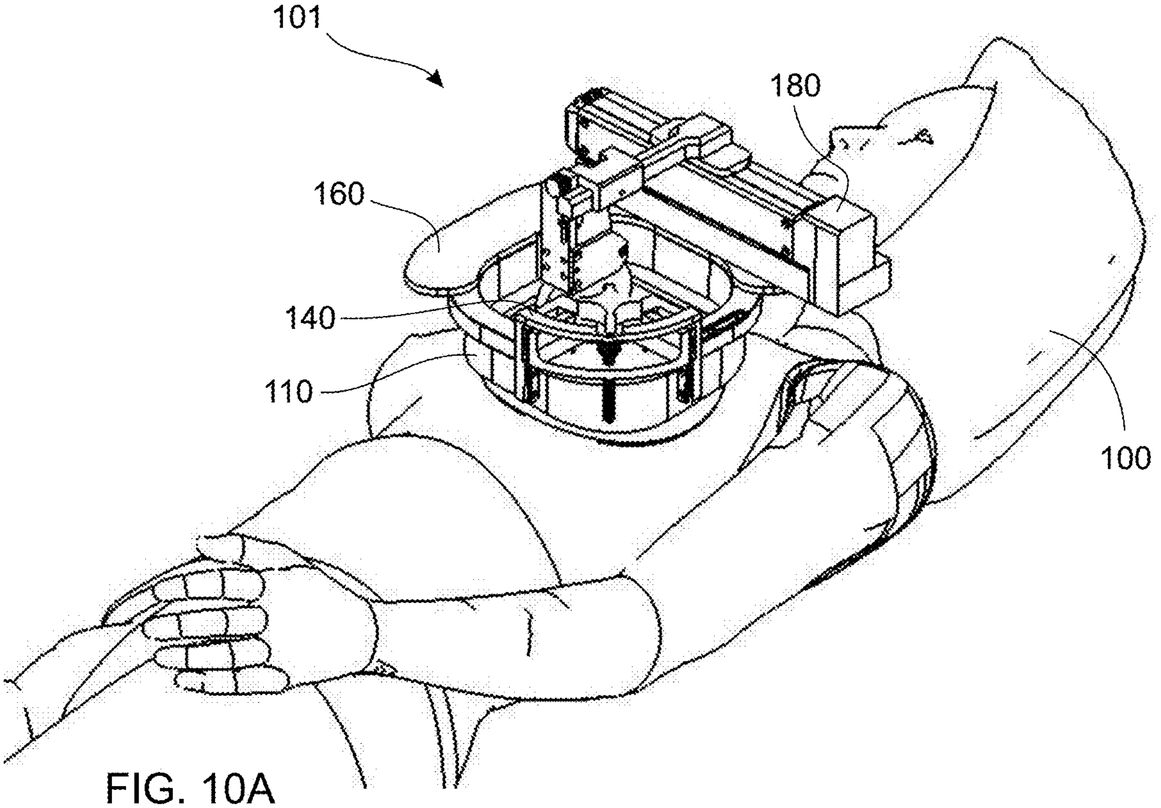
FIG. 10A depicts the imaging system of FIG. 9 mounted on a left breast of a subject.
Figure 10B:
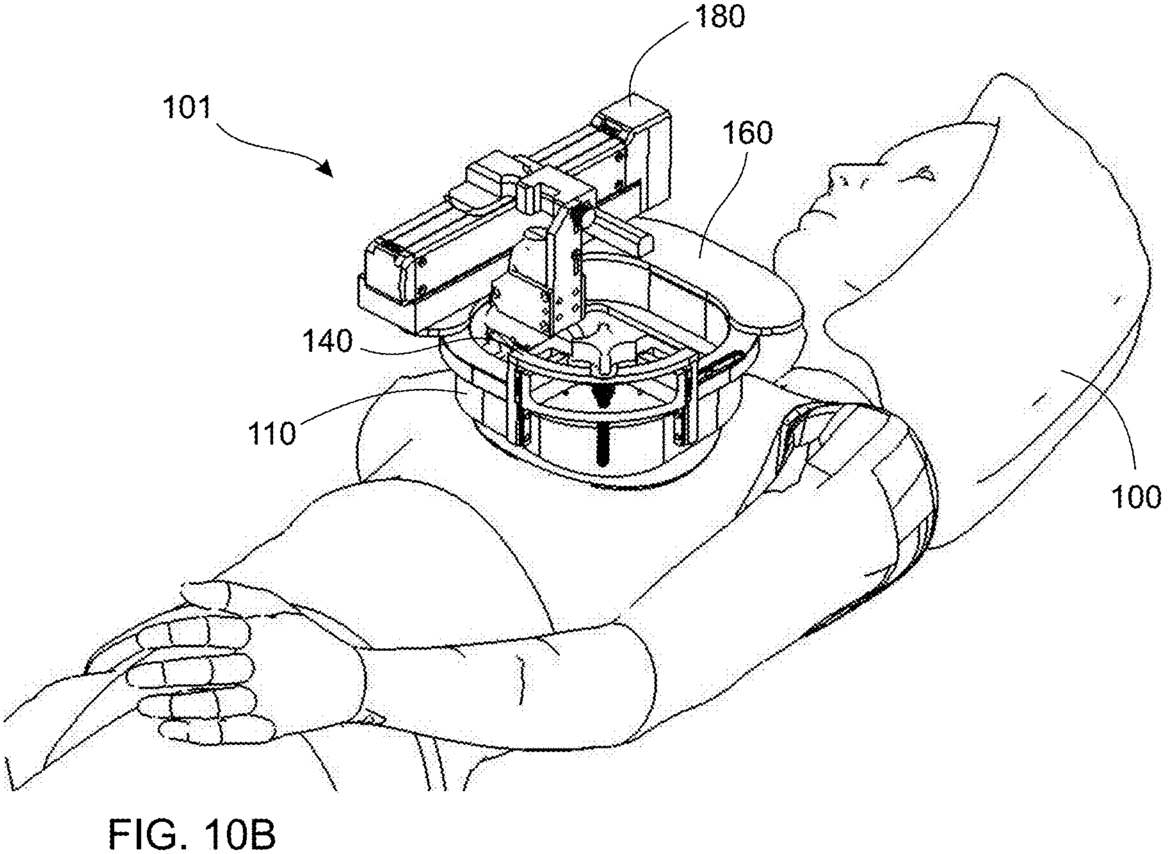
FIG. 10B depicts a similar view as FIG. 10A except that a motor plate subassembly is oriented at 90° to the orientation shown in FIG. 10A.
Figure 11A:
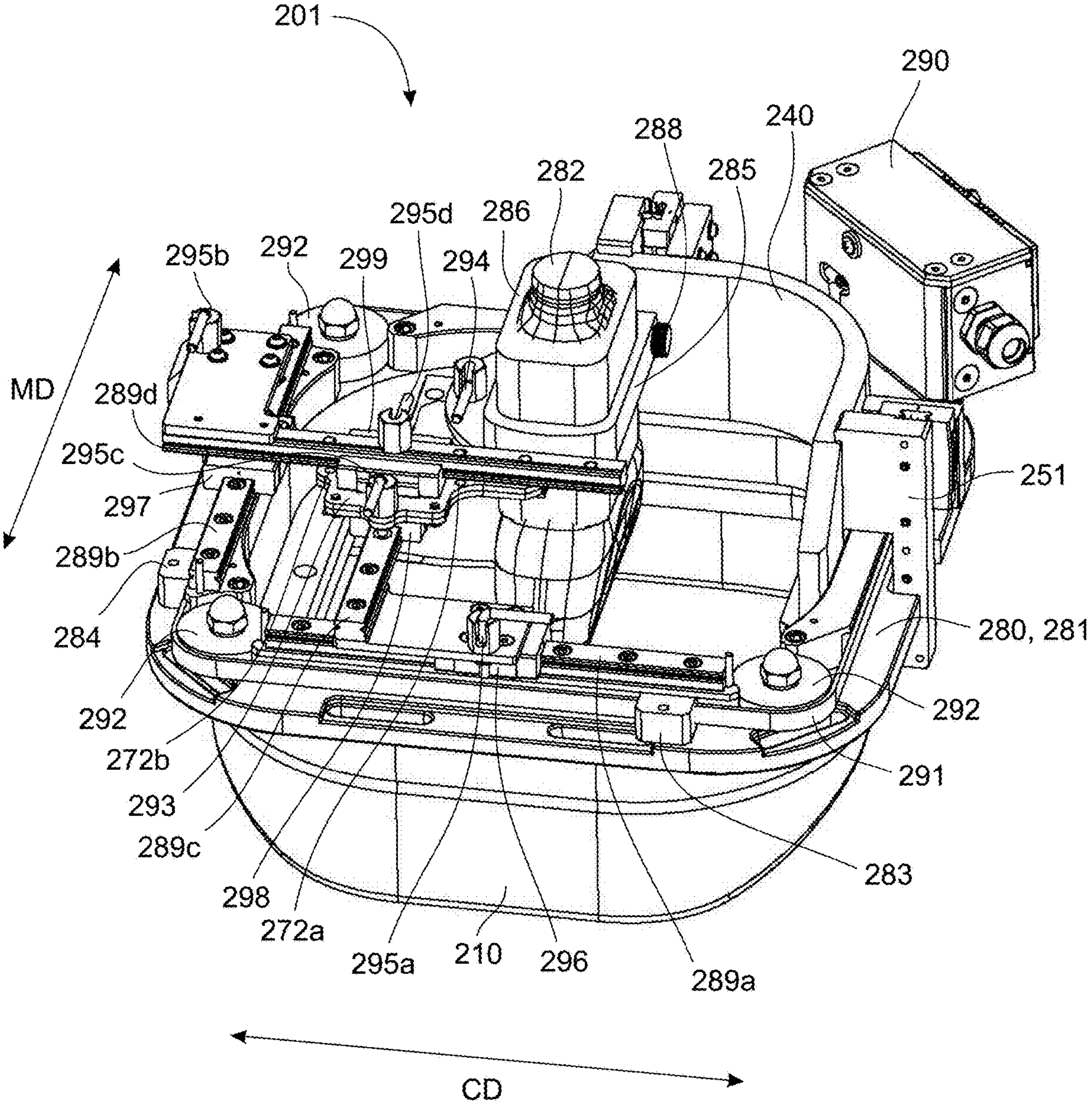
FIG. 11A depicts another embodiment of a whole breast 3D ultrasound imaging system.
Figure 11B:
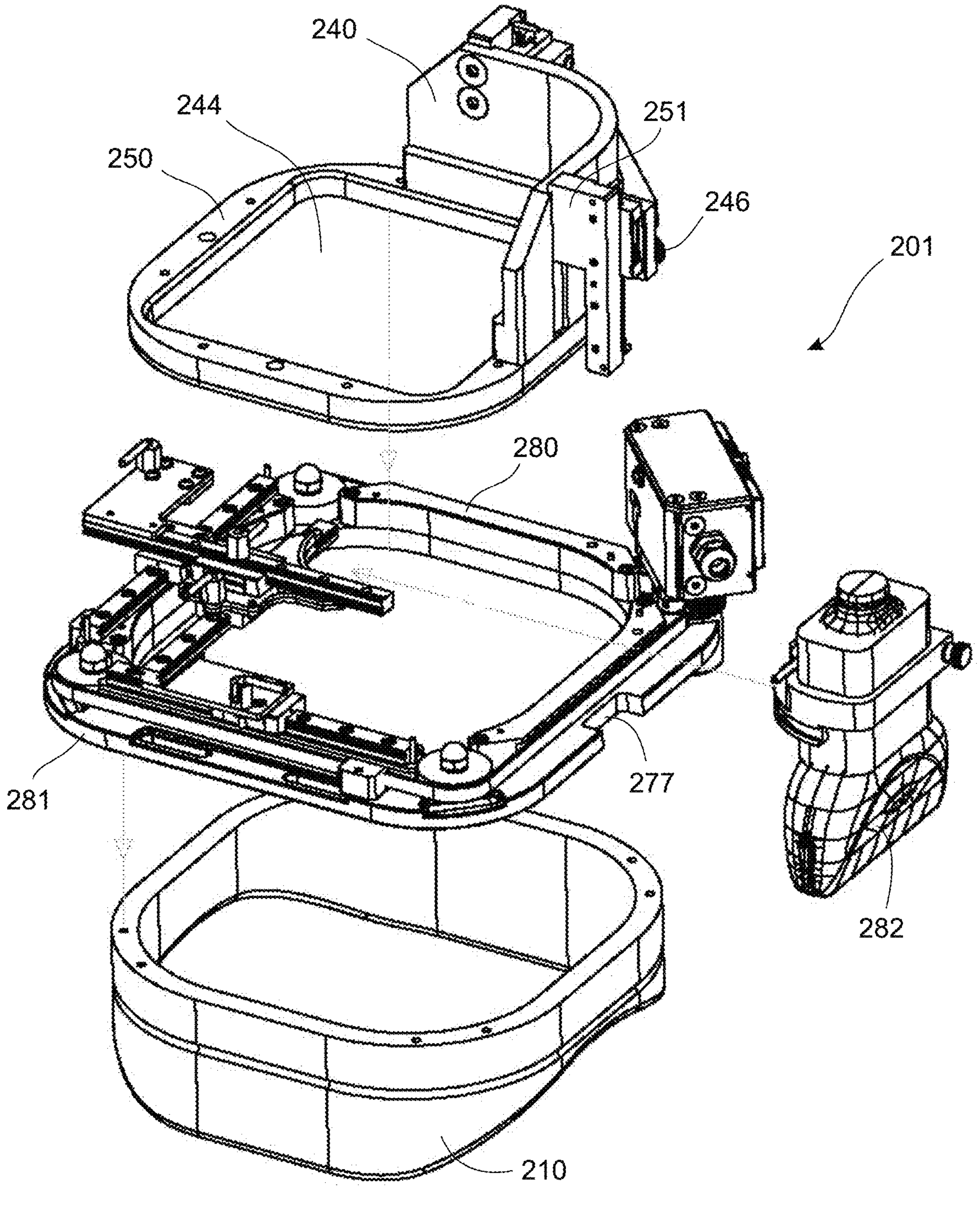
FIG. 11B depicts an exploded view of FIG. 11A.

With reference to FIG. 9, FIG. 10A and FIG. 10B, another embodiment of a whole breast 3D ultrasound imaging system 101 comprises three subassemblies including a wearable adapter subassembly 110, a compression plate subassembly 140 and a motor plate subassembly 180. The compression plate subassembly 140 is releasably mountable on the wearable adapter subassembly 110. The motor plate subassembly 180 is also releasably mountable on the wearable adapter subassembly 110. Thus, the imaging system 101 is modular in a similar manner to the imaging system 1.

The wearable adapter subassembly 110 is essentially the same as the wearable adapter subassembly 10 of the imaging system 1. The wearable adapter subassembly 110 therefore comprises an annular wall defining a volume for containing ultrasound transmission around a breast of a subject during operation of the ultrasound imaging system 101. The wearable adapter subassembly 110 is also worn by the subject 100 using adjustable straps through slots 120 in a lip of the upper edge of the annular wall. A lower edge of the annular wall is also provided with a compressible gasket 115.

The compression plate subassembly 140 is releasably mounted on an upper edge of the annular wall of the wearable adapter subassembly 110 and secured to the upper edge via a clamping screw 141 through a threaded mounting aperture in the lip of the upper edge. The compression plate subassembly 140 comprises a compression plate 144 mounted to a threaded mounting bolt 152 connected to an adjustment knob 154, the compression plate 144 mounted within the volume defined by the annular wall of the wearable adapter subassembly 110. The mounting bolt 152 is threaded through a threaded aperture in an upper surface of the compression plate subassembly 140 whereby rotation of the adjustment knob 154, and therefore rotation of the mounting bolt 152 in the threaded aperture, causes the compression plate 144 to raise and lower as desired. Because the compression plate subassembly 140 is small, occupying only a small portion of the upper edge of the annular wall of the wearable adapter subassembly 110, only a single clamping screw 141 and a single mounting bolt 152 are required.

The motor plate subassembly 180 is releasably mounted on the wearable adapter subassembly 110 instead of the compression plate subassembly 140. The motor plate subassembly 180 may be mounted directly to the upper edge of the annular wall of the wearable adapter subassembly 110, but in the illustrated embodiment, the motor plate subassembly 180 is mounted on an interface plate 160, which is releasably mounted on the upper edge of the annular wall of the wearable adapter subassembly 110. The interface plate 160 may be fixedly mounted or releasably mounted on the wearable adapter subassembly 110. The motor plate subassembly 180 is releasably mounted on the interface plate 160 by virtue of mounting pins (not shown) on a lower face of the motor plate subassembly 180 indexed to locating apertures 167 in an upper surface of or through the interface plate 160. The interface plate 160 is curved and comprises locating apertures 167 on both transverse and longitudinal sections of the curve so that the motor plate subassembly 180 can be simply picked up, after operating a release pin 183, and re-oriented by 90° on the interface plate 160, as seen in FIG. 10A and FIG. 10B. The release pin 183 holds the motor plate subassembly 180 to the interface plate 160.

In some embodiment, the interface plate 160 can be considered a non-moving part of the compression plate subassembly 140, especially if the interface plate 160 is directly connected to the compression plate subassembly 140. However, it is a feature of the imaging system 101 that the motor plate subassembly 180 does not move synchronously with the compression plate 144. Thus, wherever the motor plate subassembly 180 is mounted, the motor plate subassembly 180 is stationary when the compression plate 144 is adjusted to contact the breast.

The motor plate subassembly 180 comprises a carriage 187 having a track 189 thereon. A slider block 186 is slidably mounted on the track 189 and is capable of being slid manually along a longitudinal axis of the carriage 187. In some embodiments, the slider block may be motorized. The slider block 186 supports a slider arm 186 that extends away from the carriage 187 to a position over the compression plate 144. The slider arm 186 supports a cradle 191, which is connected to a mounting bracket 185 to which an ultrasound transducer 182 is mounted. A long axis of the ultrasound transducer 182 is mounted perpendicular to a direction of travel of the slider block 186 do that sliding the slider block 186 translates the ultrasound transducer 182 along the compression plate 144 to acquire 2D images or a series of 2D images. Because the motor plate subassembly 180 does not move with the compression plate 144, height adjustment of the ultrasound transducer 182 may be required to make ultrasonic contact with the breast of the subject 100. Height adjustment can be accomplished by the operating a height adjusting fitting 188, which is a knobbed screw holding the ultrasound transducer 182 to the mounting bracket 185, the knobbed screw loosenable and tightenable in a slot in the mounting bracket 185. By changing the orientation of the motor plate subassembly 180 on the wearable adapter subassembly 110 by 90° (see FIG. 10A and FIG. 10B), the orientation of the ultrasound transducer 182 can be changed by 90° so that a second scan can be taken orthogonally to a first scan and the scan results stitched together by a computer to produce 3D images or a series of 3D images.

Another embodiment of a whole breast 3D ultrasound imaging system 201 is illustrated in FIG. 11A to FIG. 15B where the whole breast 3D ultrasound imaging system 201 comprises three subassemblies including a wearable adapter subassembly 210 made from a rapid-prototype 3D-printed dam, a compression plate subassembly 240 and a motor plate subassembly 280 releasably stackable with each other with the compression plate subassembly 40 situated above the wearable adapter subassembly 210.

The compression plate subassembly 240 comprises a generally rectangular frame 250 and an ultrasound compression plate 244 mounted to and underneath the frame 250. The frame 250 comprises a mounting bracket 251 that engages the motor plate subassembly 280 at a detent 277 in the motor plate subassembly 280. The position of the frame

250, and therefore the position of the ultrasound compression plate 244, relative to the positions of the wearable adapter subassembly 210 and the motor plate subassembly 280 can be adjusted by clamping the frame 250 at different positions on the motor plate subassembly 280 using a clamping knob 246.

The motor plate subassembly 280 comprises a motor plate 281 having a generally rectangular shape. The motor plate 281 has a motor 290 mounted thereon at one of the corners of the motor plate 281. The motor 290 drives a timing belt 291 around three pullies 292 situated at each of the other corners of the mounting plate 281. Rigidly attached to the timing belt 291 are a craniocaudal coupling 283 and a mediolateral coupling 284. An ultrasound transducer 282 may be coupled to either the craniocaudal coupling 283 or the mediolateral coupling 284. Coupling the ultrasound transducer 282 to the craniocaudal coupling 283 permits creating multiple scans in a craniocaudal direction CD without removing the ultrasound transducer 282 or motor plate 281 between scans. Coupling the ultrasound transducer 282 to the mediolateral coupling 283 permits creating multiple scans in a mediolateral direction MD without removing the ultrasound transducer 282 or the motor plate 281 between scans.

Figure 12D:
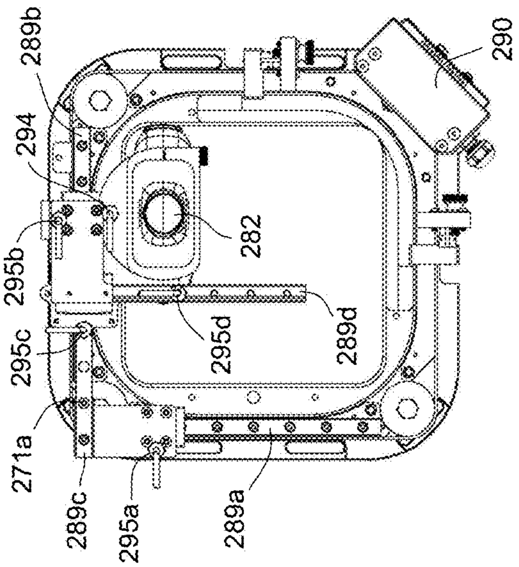
Figure 13A:
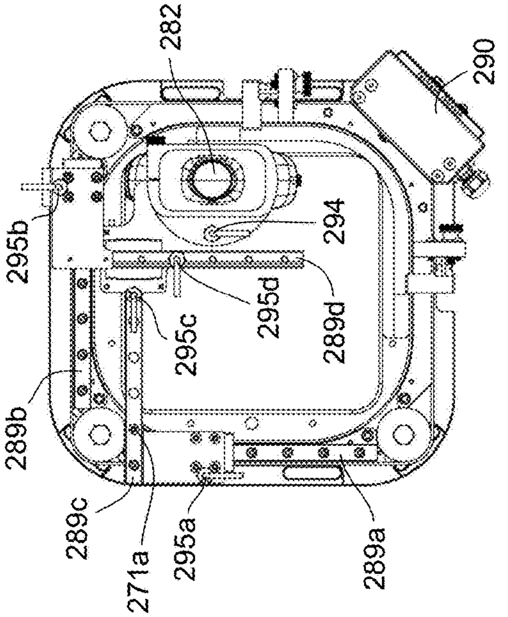
FIG. 13A, FIG. 13B, FIG. 13C and FIG. 13D depict a series of top views of the whole breast 3D ultrasound imaging system of FIG. 11A showing how an ultrasound transducer is translated in a mediolateral direction during a scan.

The ultrasound transducer 282 is held in place by a cradle 286, which is slidably connected to a cradle adapter 285 along a long axis of the ultrasound transducer 282 (i.e., same direction as the cord of the ultrasound transducer). The cradle 286 can be fixed in place by cradle knob 288 once the ultrasound transducer 282 is in contact with the compression plate 244 which in turn is in contact with a patient's skin. The cradle adapter 285 is coupled to a cross rail mounting block 293 in a manner where the ultrasound transducer 282 can pivot about the long axis of the transducer 282 allowing a maximum of 90 degrees of adjustment needed to scan either in the craniocaudal direction CD or the mediolateral direction MD where the ultrasound imaging plane is at right angles to the direction of the scan. A spring-loaded locking pin 294 constrains the ultrasound transducer 282 in one of two possible orientations as best shown in FIG. 12*d* and FIG. 13A.

The cross rail mounting block 293 is rigidly connected to two linear bearing blocks 298, 299 which are mounted to each other at right angles and are parallel to rails 289*a* and 289*b* which define the scanning directions CD and MD. The bearing blocks 298 and 299 are slidably connected to two rails 289*c* and 289*d* which in turn are rigidly connected to bearing blocks 296 and 297. The two rails 289*c* and 289*d* are mounted at right angles to the direction of travel of rails 289*a* and 289*b*. This gives the ultrasound transducer 282 the ability to move freely with 2 degrees of freedom in either of the scan directions CD and MD unless constrained by one of a plurality of spring-loaded locking pins 295*a*. 295*b*, 295*c*, 295*d* associated with the respective rails 289*a*, 289*b*, 289*c*, 289*d* when the imaging system 201 is used for scanning. The location of the bearing block 298 is constrained on the rail 289*c* when the locking pin 295*c* engages with one of two apertures 271*a* or 271*b* and the location of the bearing block 299 is constrained on the rail 289*d* when the locking pin 295*d* engages with one of two apertures 272*a* or 272*b*. The locking pins 295*a* and 295*b* are used to couple transducer motion to either the craniocaudal direction CD or the mediolateral MD direction, which is driven by the motor 290. The locking pins 295*c* and 295*d* are used to constrain the ultrasound transducer 282 in one of two positions along the rails 289*c* and 289*d*.

FIG. 12A to FIG. 12D, FIG. 13A to FIG. 13D, FIG. 14A and FIG. 14B illustrate how multiple scans can be created. FIG. 12A to FIG. 12D and FIG. 14A show how two parallel scans can be created along the craniocaudal direction CD where the user would set the ultrasound transducer 282 in position A1 (see FIG. 12A for detail) where the locking pin 295*a* is engaged with the craniocaudal coupling 283. The first 3D scan is created when the motor 290 moves the ultrasound transducer 282 from position A1 to position A2. The user would then reposition the ultrasound transducer 282 to positions A3 by releasing the locking pin 295*c* from the aperture 271*a* and then engaging the locking pin 295*c* with the aperture 271*b*. The second scan is created when the ultrasound transducer 282 is moved from position A3 to position A4, thus creating two parallel scans that can be stitched together electronically to form one larger image.

Figure 12A:
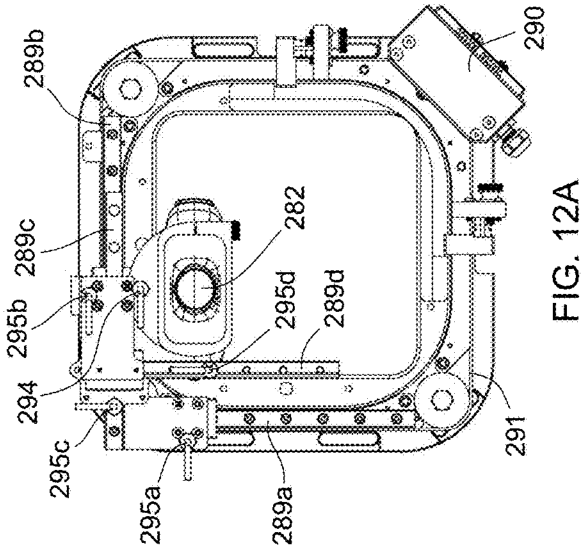
FIG. 12A, FIG. 12B, FIG. 12C and FIG. 12D depict a series of top views of the whole breast 3D ultrasound imaging system of FIG. 11A showing how an ultrasound transducer is translated in a craniocaudal direction during a scan.
Figure 12B:
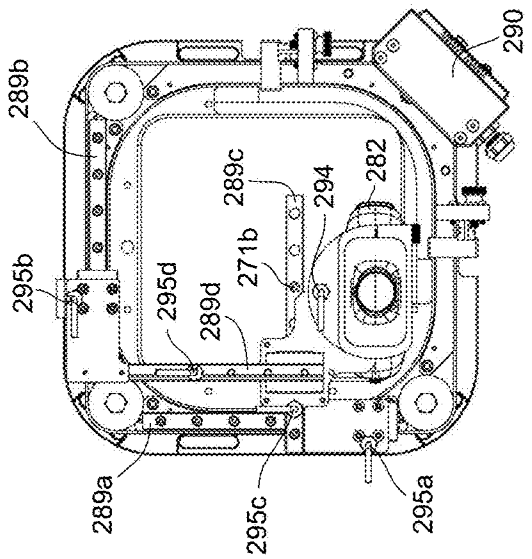
Figure 12C:
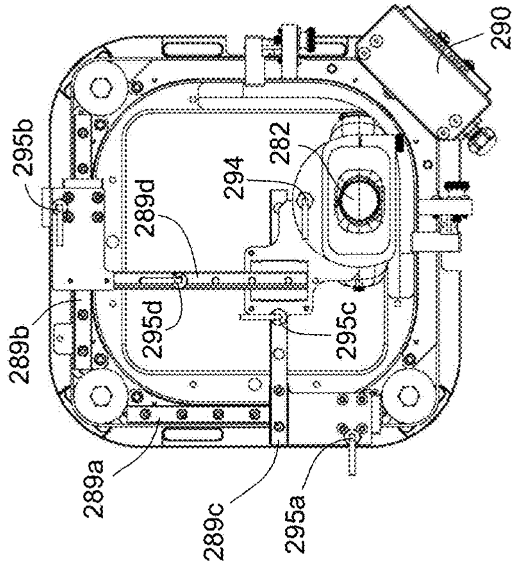

With reference to FIG. 12A to FIG. 12D, details of ultrasound transducer positioning and locking pin engagement during a craniocaudal scan are summarized as follows:

- FIG. 12A: Craniocaudal scan, ultrasound transducer 282 upper right (near the patient head): detail of the ultrasound transducer 282 in position A1 as shown in FIG. 14A. Locking pins 295*c* and 295*a* are engaged while locking pins 295*b* and 295*d* are released. The locking pin 295*c* is engaged in a position defined by aperture 271*a*.
- FIG. 12B: Craniocaudal scan, ultrasound transducer 282 lower right (away from the patient head): detail of the ultrasound transducer 282 in position A2 as shown in FIG. 14A. Locking pins 295*c* and 295*a* are engaged while locking pins 295*b* and 295*d* are released.
- FIG. 12C: Craniocaudal scan, ultrasound transducer 282 lower left: detail of the ultrasound transducer 282 in position A3 as shown in FIG. 14A. Locking pins 295*c* and 295*a* are engaged while locking pins 295*b* and 295*d* are released. The locking pin 295*c* is engaged in a position defined by aperture 271*b*.
- FIG. 12D: Craniocaudal scan, ultrasound transducer 282 upper left: detail of the ultrasound transducer 282 in position A4 as shown in FIG. 14A. Locking pins 295*c* and 295*a* are engaged while locking pins 295*b* and 295*d* are released.

Figure 13B:
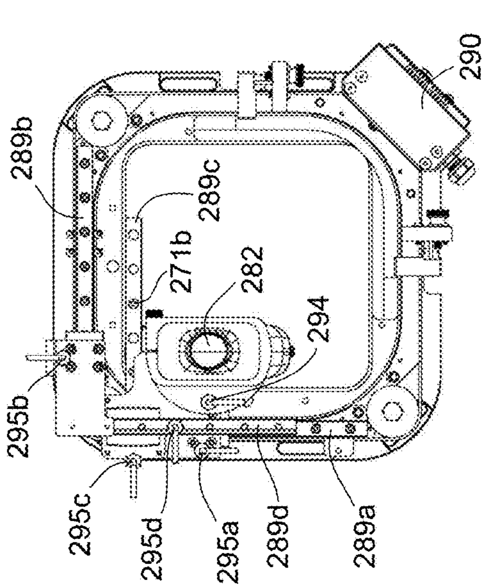
Figure 13C:
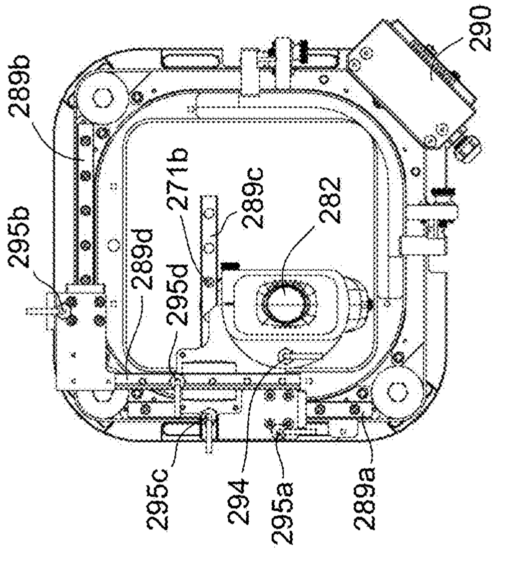
Figure 13D:
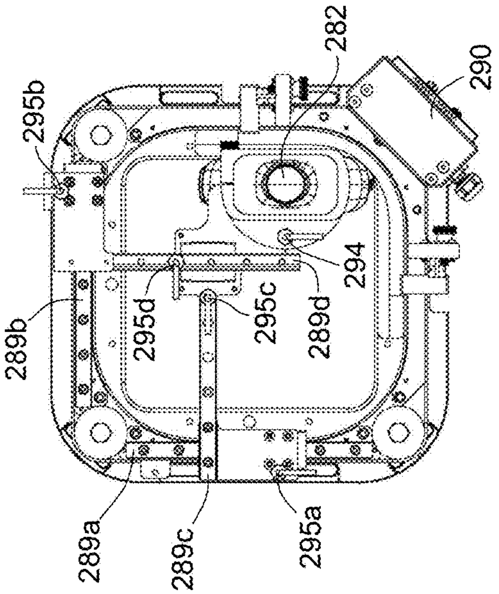
Figure 14B:
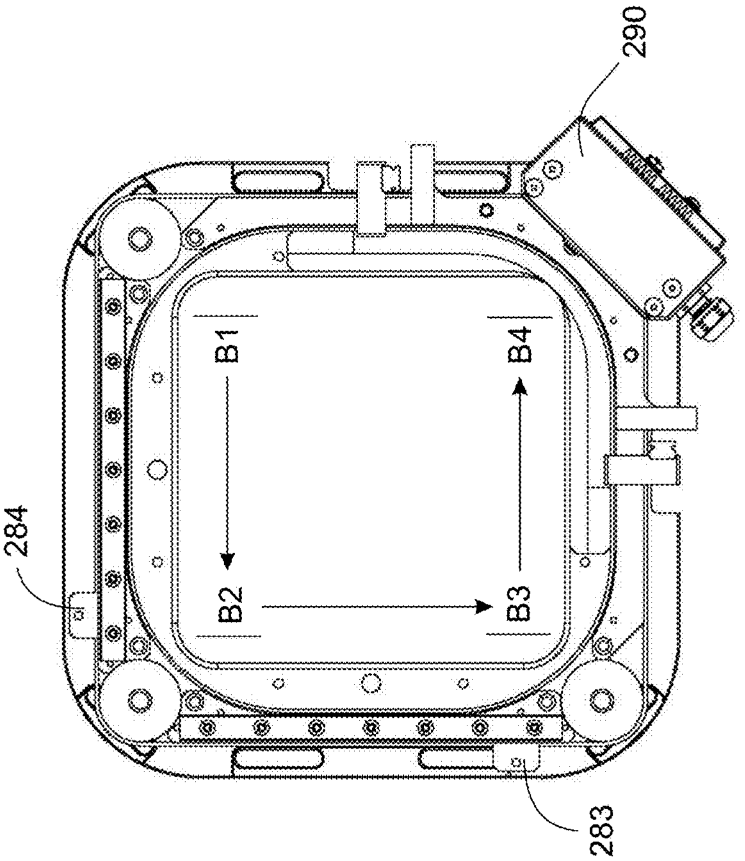
FIG. 14A and FIG. 14B illustrate schematically how multiple scans can be created with the whole breast 3D ultrasound imaging system of FIG. 11A.
Figure 14A:
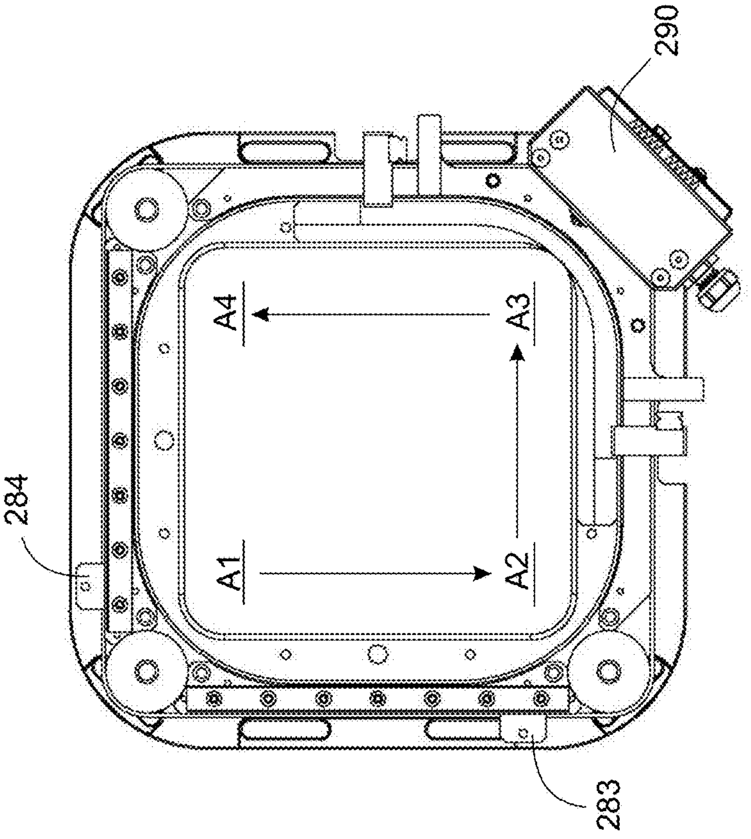

FIG. 13A to FIG. 13D and FIG. 14B show how two parallel scans can be created along the mediolateral direction MD. To create two additional scans at right angles to the first two images, the ultrasound transducer 282 is set up in position B1 as shown in FIG. 14B. The ultrasound transducer 282 is rotated 90 degrees relative to position A4 by releasing the locking pin 294, turning the ultrasound transducer 282, and re-engaging the locking pin 294 to lock the orientation. To engage transducer motion into the mediolateral direction MD, the locking pins 295*a* and 295*c* are released, the locking pin 295*b* is engaged in an aperture in the mediolateral coupling 284, and the locking pin 295*d* is locked in aperture 272*a*. The third 3D scan is created when the motor 290 moves the ultrasound transducer 282 from position B1 to position B2. The user would then reposition the ultrasound transducer 282 in position B3 by releasing the locking pin 295*d* from the aperture 272*a* and engaging the locking pin 295*d* with aperture 272*b*. The fourth scan is created when the ultrasound transducer 282 is moved from position B3 to position B4, thus creating two parallel scans that can be stitched together electronically to form one larger image and can be merged with the first two scans to improve the resolution of the final image by combining two 3D images where the scan directions are at right angles.

With reference to FIG. 13A to FIG. 13D, details of ultrasound transducer positioning and locking pin engagement during a mediolateral scan are summarized as follows:

FIG. 13A: Mediolateral scan, ultrasound transducer 282 upper left: detail of the ultrasound transducer 282 in position B1 as shown in FIG. 14B. Locking pins 295*c* and 295*a* are released while locking pins 295*b* and 295*d* are engaged. The locking pin 295*d* is engaged in a position defined by aperture 272*a*. In addition, the ultrasound transducer 282 is rotated 90 degrees relative to position A4 by releasing the locking pin 294, repositioning the ultrasound transducer 282, and re-engaging the locking pin 294.

FIG. 13B: Mediolateral scan, ultrasound transducer 282 upper right: detail of the ultrasound transducer 282 in position B2 as shown in FIG. 14B. Locking pins 295*c* and 295*a* are released while locking pins 295*b* and 295*d* are engaged.

FIG. 13C: Mediolateral scan, ultrasound transducer 282 lower right: detail of the ultrasound transducer 282 in position B3 as shown in FIG. 14B. Locking pins 295*c* and 295*a* are released while locking pins 295*b* and 295*d* are engaged. The locking pin 295*d* is engaged in a position defined by the aperture 272*b*.

FIG. 13D: Mediolateral scan, ultrasound transducer 282 lower left: detail of the ultrasound transducer 282 in position B4 as shown in FIG. 14B. Locking pins 295*c* and 295*a* are released while locking pins 295*b* and 295*d* are engaged.

Figure 15A:
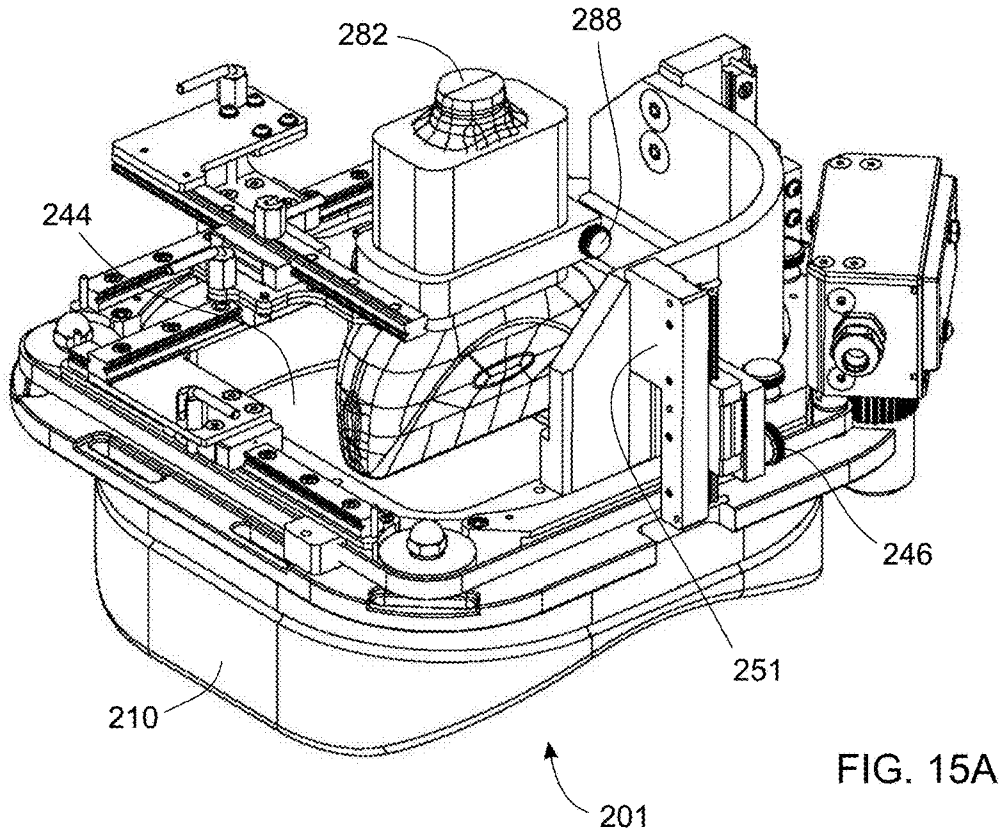
FIG. 15A depicts the whole breast 3D ultrasound imaging system of FIG. 11A with a compression plate and an ultrasound transducer in a raised position.
Figure 15B:
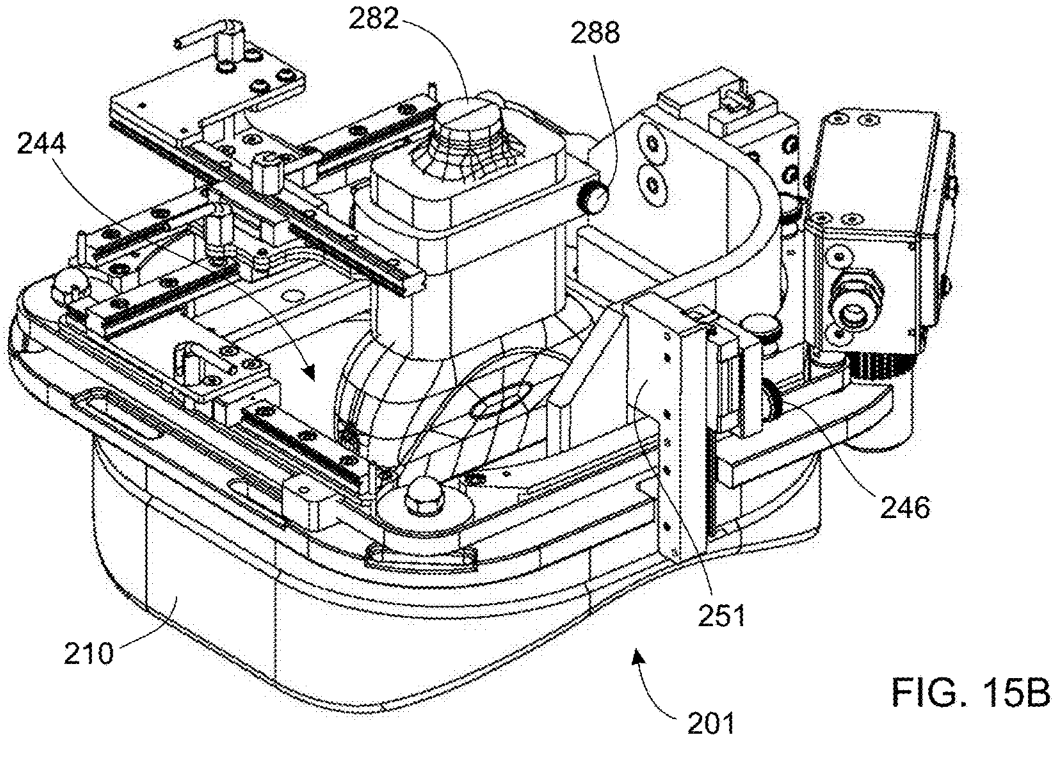
FIG. 15B depicts the whole breast 3D ultrasound imaging system of FIG. 11A with a compression plate and an ultrasound transducer in a lowered position.

FIG. 15A and FIG. 15B illustrate the imaging system 201 with the ultrasound transducer 282 and the compression plate 244 in raised and lowered positions, respectively. The ultrasound transducer 282 and the compression plate 244 can be raised and lowered to accommodate different breast sizes. The cradle knob 288 is used to unlock and lock the cradle 286 to permit and prevent sliding of the cradle 286 in the cradle adapter 285 to raise and lower the ultrasound transducer 282. Likewise, the clamping knob 246 is used to unlock and lock the mounting bracket 251 of the frame 250 to permit and prevent movement of the frame 250 to raise and lower the compression plate 244.

The novel features will become apparent to those of skill in the art upon examination of the description. It should be understood, however, that the scope of the claims should not be limited by the embodiments but should be given the broadest interpretation consistent with the wording of the claims and the specification as a whole.

The invention claimed is:

1. A method of obtaining a whole breast 3D ultrasound image, the method comprising:

placing an adapter subassembly of a whole breast 3D ultrasound imaging system around a whole breast of a subject, the adapter subassembly comprising an annular wall for containing an ultrasound transmission fluid around the breast of the subject;

fastening the adapter subassembly to the subject to provide a seal between a first edge of the annular wall and a body surface around the breast of the subject to reduce leakage of the ultrasound fluid between the first edge and the body surface of the subject;

providing the ultrasound transmission fluid inside the annular wall of the adapter subassembly around the breast of the subject;

releasably mounting a compression plate subassembly of the whole breast 3D ultrasound imaging system on a second edge of the adapter subassembly thereby positioning an ultrasound compression plate of the compression plate subassembly above the breast with the ultrasound fluid between the compression plate and the body surface of the subject;

adjusting a height of the compression plate to compress the breast;

releasably mounting a motor plate subassembly of the whole breast 3D ultrasound imaging system on the adapter subassembly or the compression plate subassembly, the motor plate subassembly comprising an ultrasound transducer movable relative to the motor plate subassembly; and, scanning the breast with the ultrasound transducer by moving the ultrasound transducer in a plane parallel to the ultrasound compression plate, wherein the compression plate subassembly comprises:

a securement portion configured to be releasably secured to the second edge of the annular wall of the adapter subassembly, and a frame with the ultrasound compression plate mounted to the frame, whereby the ultrasound compression plate is height adjustable relative to the securement portion, wherein the frame comprises mounting bolts secured thereon, the mounting bolts engaging the securement portion to connect the frame to the securement portion, wherein to adjust the height of the compression plate, at least one of the mounting bolts is rotated in a threaded aperture in the securement portion to cause the frame and the ultrasound compression plate to move relative to the securement portion when the securement portion is secured on the adapter subassembly.

2. The method of claim 1, wherein the ultrasound fluid directly contacts the breast.

3. The method of claim 1, wherein the adapter subassembly further comprises a flexible membrane covering a lower open face of the adapter subassembly, the flexible membrane deformed by the breast when the breast is housed within the annular wall.

4. The method of claim 1, wherein the adapter subassembly comprises a compressible gasket on the first edge to assist with providing the seal between the first edge and the body surface of the subject.

5. The method of claim 1, wherein the adapter subassembly comprises a hinge permitting the annular wall to flex to assist with providing the seal between the first edge and the body surface of the subject.

6. The method of claim 2, wherein the adapter subassembly comprises a compressible gasket made of an elastomeric material on the first edge to assist with providing the seal between the first edge and the body surface of the subject.

7. The method of claim 6, wherein the adapter subassembly comprises a hinge permitting the annular wall to flex to assist with providing the seal between the first edge and the body surface of the subject.

8. The method of claim 1, wherein the adapter subassembly is fastened to the subject with adjustable straps.

9. The method of claim 6, wherein the adapter subassembly is fastened to the subject with adjustable straps and wherein the straps are adjusted to compress the compressible gasket relative to the body surface of the subject.

10. The method of claim 7, wherein the adapter subassembly is fastened to the subject with adjustable straps, wherein the straps are adjusted to compress the compressible gasket relative to the body surface of the subject, and wherein the straps are adjusted to cause the annular wall to flex.

11. The method of claim 1, wherein the adapter subassembly moves with the subject when the subject moves in any direction.

12. The method of claim 1, wherein the compression plate subassembly is between the adapter subassembly and the motor plate subassembly.

13. The method of claim 1, wherein the motor plate subassembly further comprises an actuator operatively coupled to the ultrasound transducer to translate the ultrasound transducer.

14. The method of claim 1, wherein the mounting bolts are all threaded and the mounting bolts are linked to each other by a timing belt so that rotation of one of the mounting bolts causes all the mounting bolts to rotate thereby causing the frame and the ultrasound compression plate to move relative to the securement portion.

15. The method of claim 1, wherein the securement portion comprises mounting screws that are threadingly mated with corresponding threaded mounting apertures in the second edge of the adapter subassembly to releasably secure the compression plate subassembly to the adapter subassembly.

16. The method of claim 1, wherein the motor plate subassembly is mounted on the frame and moves with the compression plate while adjusting the height of the compression plate.

* * * * *